United States Patent
Bodduluri et al.

(10) Patent No.: US 8,545,517 B2
(45) Date of Patent: Oct. 1, 2013

(54) SYSTEMS AND METHODS FOR IMPROVING FOLLICULAR UNIT HARVESTING

(75) Inventors: Mohan Bodduluri, Palo Alto, CA (US);
Joseph A. Heanue, Oakland, CA (US);
Kate L. Bechtel, Berkeley, CA (US);
Brian P. Wilfley, Los Altos, CA (US)

(73) Assignee: Restoration Robotics, Inc., San Jose, CA (US)

( * ) Notice: Subject to any disclaimer, the term of this patent is extended or adjusted under 35 U.S.C. 154(b) by 1127 days.

(21) Appl. No.: 12/477,444

(22) Filed: Jun. 3, 2009

(65) Prior Publication Data
US 2009/0306498 A1   Dec. 10, 2009

Related U.S. Application Data

(60) Provisional application No. 61/059,476, filed on Jun. 6, 2008.

(51) Int. Cl.
*A61B 17/50* (2006.01)
*A61B 5/107* (2006.01)
*G05B 15/00* (2006.01)

(52) U.S. Cl.
USPC .......................... 606/133; 700/259

(58) Field of Classification Search
USPC . 606/131, 133, 185, 187, 1, 9; 382/254–275, 382/128, 153; 600/407–458; 700/245–264
See application file for complete search history.

(56) References Cited

U.S. PATENT DOCUMENTS

| | | | |
|---|---|---|---|
| 5,941,827 A | 8/1999 | Papaioannou | |
| 6,013,087 A | 1/2000 | Adams et al. | |
| 6,230,046 B1 | 5/2001 | Crane et al. | |
| 6,572,625 B1 | 6/2003 | Rassman | |
| 6,585,746 B2 | 7/2003 | Gildenberg | |
| 6,949,115 B2 | 9/2005 | Mascio | |
| 7,217,266 B2 | 5/2007 | Anderson et al. | |
| 7,239,909 B2 | 7/2007 | Zeman | |
| 7,627,157 B2 | 12/2009 | Qureshi et al. | |

(Continued)

FOREIGN PATENT DOCUMENTS

WO   2005/062938   7/2005

OTHER PUBLICATIONS

Gladimair V. G. Baranoski; Aravind Krishnaswamy. "An Introduction to Light Interaction with Human Skin". RITA. vol. XI, Numero 1, 2004 (pp. 33-62).

(Continued)

*Primary Examiner* — Kathleen Holwerda
*Assistant Examiner* — Sarah W Aleman
(74) *Attorney, Agent, or Firm* — Lena I. Vinitskaya; Sharon Upham

(57) ABSTRACT

Tools and methods are provided for dissecting and/or removing biological units, such as hair follicles, from the body surface based on the images both above and below a body surface to reduce potential damage to the removed biological unit. The invention may be used in fully automated systems and also in a hand-held devices and systems. A system may produce a series of three-dimensional images of the body surface indicating follicular unit size, shape, position, and orientation both above and below the skin surface. The images may be utilized by an automated follicular unit harvesting tool, or maybe stored for later use. Imaging techniques include devices that sense light in the visible or infrared spectrums, optical coherence tomography, and ultrahigh frequency ultrasound.

33 Claims, 9 Drawing Sheets

(56) References Cited

U.S. PATENT DOCUMENTS

| | | | |
|---|---|---|---|
| 2001/0008959 A1* | 7/2001 | Nemati | 604/20 |
| 2002/0103500 A1 | 8/2002 | Gildenberg | |
| 2003/0120298 A1 | 6/2003 | Gildenberg | |
| 2005/0154431 A1 | 7/2005 | Quistgaard et al. | |
| 2006/0079816 A1 | 4/2006 | Barthe et al. | |
| 2007/0012135 A1* | 1/2007 | Tierney et al. | 74/490.01 |
| 2007/0038118 A1 | 2/2007 | DePue et al. | |
| 2007/0071354 A1* | 3/2007 | Florent et al. | 382/266 |
| 2007/0106306 A1* | 5/2007 | Bodduluri et al. | 606/133 |
| 2007/0106307 A1 | 5/2007 | Bodduluri et al. | |
| 2007/0149985 A1 | 6/2007 | Cole | |
| 2007/0238954 A1* | 10/2007 | White et al. | 600/407 |
| 2008/0002809 A1 | 1/2008 | Bodduluri | |
| 2008/0049993 A1* | 2/2008 | Qureshi et al. | 382/128 |
| 2008/0242990 A1 | 10/2008 | Zanelli et al. | |

OTHER PUBLICATIONS

S. Bourquin; V. Monterosso; and P. Seitz. "Video-Rate Optical Low-Coherence Reflectometry Based on a Linear Smart Detector Array". Optics Letters. vol. 25, No. 2, Jan. 15, 2000. (pp. 102-104).

Pete J. Burt and Edward H. Adelson. "The Laplacian Pyramid as a Compact Image Code". IEEE Transactions on Communications, vol. Com-3I, No. 4, Apr. 1983. (pp. 532-540).

Michael A. Choma; Marinko V. Sarunic; Changhuei Yang; Joseph A. Izatt. "Sensitivity Advantage of Swept Source and Fourier Domain Optical Coherence Tomography". Optics Express. vol. 11, No. 18, Sep. 8, 2003. (pp. 2183-2189).

Joris J. J. Dirckx; Liesbeth C. Kuypers; Willem F. Decraemer. "Refractive Index of Tissue Measured with Confocal Microscopy". Journal of Biomedical Optics 10(4), 044014 (Jul./Aug. 2005).

Wolfgang Drexler. "Ultrahigh-Resolution Optical Coherence Tomography". Journal of Biomedical Optics 9(1). Jan./Feb. 2004. pp. 47-74.

A. F. Fercher; W. Drexler; C. K. Hitzenberger and T. Lasser. "Optical Coherence Tomography—Principles and Applications". Institute of Physics Publishing. Rep. Prog. Phys. 66 (2003) (pp. 239-303).

James G. Fujimoto. "Optical Coherence Tomography for Ultrahigh Resolution In Vivo Imaging". Nature Publishing Group. Nature Biotechnology. vol. 21, No. 11, Nov. 2003. (pp. 1361-1367).

Gerd Hausler and Michael Walter Lindner. "'Coherence Radar' and 'Spectral Radar'—New Tools for Dermatological Diagnosis'. Journal of Biomedical Optics 3(1), Jan. 1998. (pp. 21-31).

Yonghong HE. "Dynamic Optical Clearing Effect of Tissue Impregnated with Hyperosmotic Agents and Studied with Optical Coherence Tomography". Journal of Biomedical Optics 9(1). Jan./Feb. 2004. (pp. 200-206).

Misbah H. Khan, MD; Bernard Choi, PhD; Samuel Chess, BS, Kristen M. Kelly, MD; Jerry McCullough, PhD, and J. Stuart Nelson, MD, PhD. "Optical Clearing of In Vivo Human Skin: Implications for Light-Based Diagnostic Imaging and Therapeutics". Laser in Surgery and Medicine 34 (2004). (pp. 83-85).

Vrushali R. Korde, MS; Garret T. Bonnema, MS; Wei Xu, PhD; Chetankumar Krishnamurthy, MS; James Ranger-Moore, PhD, Kathylynn Saboda, MS; Lisa D. Slayton, RN; Stuart J. Salasche, MD; James A. Warneke, MD; David S. Alberts, MD. and Jennifer K. Barton. "Using Optical Coherence Tomography to Evaluate Skin Sun Damage and Precancer". Lasers in Surgery and Medicine 39, 2007. (pp. 687-695).

Markus Laubscher; Mathieu Ducros; Boris Karamata; Theo Laser and Rene Salathe. "Video-Rate Three-Dimensional Optical Coherence Tomography". Optics Express. vol. 10, No. 9; May 6, 2002. (pp. 429-435).

Julia G. Lyubovitsky; Joel A. Spencer; Tatiana B. Krasieva; Bogi Andersen; Bruce J. Tromberg. "Imaging Corneal Pathology in a Transgenic Mouse Model using Nonlinear Microscopy". Journal of Biomedical Optics 11(1), 014013 (Jan./Feb. 2006).

Julia G. Lyubovitsky and Tatiana B. Krasieva. "In Situ Multiphoton Optical Tomography of Hair Follicles in Mice". Journal of Biomedical Optics 12(4). Jul./Aug. 2007. (pp. 044003-1 to 044003-8).

N. Otberg; H. Richter; A. Knuttel; H. Schaefer; W. Sterry and J. Lademann. "Laser Spectroscopic Methods for the Characterization of Open and Closed Follicles". Laser Phys. Lett 1. No. 1 2004 (pp. 46-49).

Yingtian Pan and Daniel L. Farkas. "Noninvasive Imaging of Living Human Skin with Dual-Wavelength Optical Coherence Tomography in Two and Three Dimensions". Journal of Biomedical Optics 3(4). Oct. 1998. (pp. 446-455).

Mark C. Pierce, John Strasswimmer, B. Hyle Park, Barrycense, and Johannes F. de Boer. "Advances in Optical Coherence Tomography Imaging for Dermatology" The Journal of Investigative Dermatology,123: Sep. 3, 2004. (pp. 458-463).

A. Gh Podoleanu, PhD. "Optical coherence tomography" The British Journal of Radiology, 78 (2005), (pp. 976-988).

Ann W. Sainter; Terry A. King; Mark R. Dickinson. "Effect of Target Biological Tissue and Choice of Light Source on Penetration Depth and Resolution in Optical Coherence Tomography". Journal of Biomedical Optics 9(1), Jan./Feb. 2004. (pp. 193-199).

Dhiraj K. Sardar and Michael L. Mayo. "Optical Characterization of Melanin". Journal of Biomedical Optics 6 (4), 404-411 (Oct. 2001).

Eero P. Simoncelli and William T. Freeman. "The Steerable Pyramid: A Flexible Architectur for Multi-Scale Derivative Computation". 2nd Annual IEEE International Conference on Image Processing. Washington, DC. Oct. 1995. (4 pages).

G. J. Tearney. "Determination of the Refractive Index of Highly Scattering Human Tissue by Optical Coherence Tomography". Optics Letters. vol. 20, No. 21 . Nov. 1, 1995. (pp. 2258-2260).

Valery V. Tuchin; Ruikang K. Wang; Alvin T. Yeh. Special Section Guest Editorial—Optical Clearing of Tissues and Cells. Journal of Biomedical Optics. Mar./Apr. 2008. vol. 13(2) (1 page).

Julia Welzel. "Optical coherence tomography in dermatology: a review". Skin Research and Technology 2001; 7. (pp. 1-9).

Jinhee Yoon; Yaeyoon Son. "Enhancement of Optical Skin Clearing Efficacy Using a Microneedle Roller". Journal of Biomedical Optics 13(2), Mar./Apr. 2008. (pp. 021103-1 to 021103-5).

S. H. Yun; G. J. Tearney; B. E. Bouma; B. H. Park and J. F. De Boer. "High-Speed Spectral-Domain Optical Coherence Tomography at 1.3 μm Wavelength". Optics Express. vol. 11, No. 26, Dec. 29, 2003. pp. 3598-3604).

Ylva Y. Grams; Lynne Whitehead; Gerda Lamers; Nico Sturmann; Joke A. Bouwstra. "On-Line Diffusion Profile of a Lipophilic Model Dye in Different Depths of a Hair Follicle in Human Scalp Skin". The Journal of Investigative Dermatology. Oct. 4, 2005. pp. 775-782.

Anthony R. Lanfranco; Andres E. Castellanos; Jaydev P. Desai; William C. Meyers. "Robotic Surgery—A Current Perspective." Annals of Surgery. vol. 239, No. 1, Jan. 2004. pp. 14-21.

James A. Harris New Methodology and Instrumentation for Follicular Unit Extraction; Lower Follicle Transection Rates and Expanded Patient Candidacy. Dermatol Surg. 32; Jan. 1, 2006. pp. 1-7.

Daniel L. Marks; Stephen A. Boppart. "Nonlinear Interferometric Vibrational Imaging". Physical Review Letters, vol. 92, No. 12, Mar. 26, 2004 (4 pages).

William R. Rassman, MD; Robert Bernstein, MD; Robert McClellan, MD; Roy Jones, MD; Eugene Worton, MD; Hendrik Uyttendaele, MD. Follicular Unit Extraction: Minimally Invasive Surgery for Hair Transplantaion. Dermatol Surg. 2002;28:720-728.

Robert M. Bernstein, MD; William R. Rassman, MD; Wojciech Szaniawski, MD; Alan J. Halperin, MC. "Follicular Transplantation". International Journal of Aesthetic and Restorative Surgery, vol. 3, No. 2, 1995, pp. 199-132.

Kurt Konolige and Davide Beymer, SRI International, SRI Small Vision System, Users Manual Software version 3.2g, Nov. 2004 (86 pages).

David A. Fosyth, Jean Ponce, "Computer Vision, A Modern Approach" 2003, Cover page, publication page, and Chapters 10 and 11, pp. 215-250.

Ramesh Jain, Rangachar Kasture, Brian G. Schunck, "Machine Vision" 1995, Cover page, publication page, and Chapters 11 and 12, pp. 289-364.

John Iselin Woodfill, Gaile Gordon, Ron Buck, "Tyzx DeepSea High Speed Stereo Vision System," Proceedings of the IEEE Computer Society Workshop on Real Time 3-D Sensors and Their Use, Conference on Computer Vision and Pattern Recognition, Jun. 2004, pp. 1-5.

Communication from Australian Patent Office, May 4, 2009 in commonly assigned Australian Patent Application No. 2006297217, which mentions US 2002/103500 [listed above on p. 2] (2 pages).

M Inaba and Y Naba. "Androgenetic Alopecia, Modern Concepts of Pathogenesis and Treatment, 29. Operative Treatment for Androgenetic Alopecia." Springer 1996, pp. 238-244.

Ramesh Jain, Rangachar Kasture, Brian G. Schunck. "Machine Vision" 1995, Cover page, publication page, and Chapters 4 and 5, pp. 112-180.

First Action Interview Pilot Program Pre-Interview Communication, mailed Jun. 17, 2010, in relation to commonly assigned U.S. Appl. No. 11/380,911 (4 pages).

First Office Action mailed Dec. 10, 2010, in relation to commonly assigned U.S. Appl. No. 11/380,911 (3 pages).

Amendment and Response to First Office Action mailed Dec. 10, 2010 in relation to commonly assigned U.S. Appl. No. 11/380,911 (10 pages).

Final Office Action mailed Mar. 28, 2011, in relation to commonly assigned U.S. Appl. No. 11/380,911 (9 pages).

\* cited by examiner

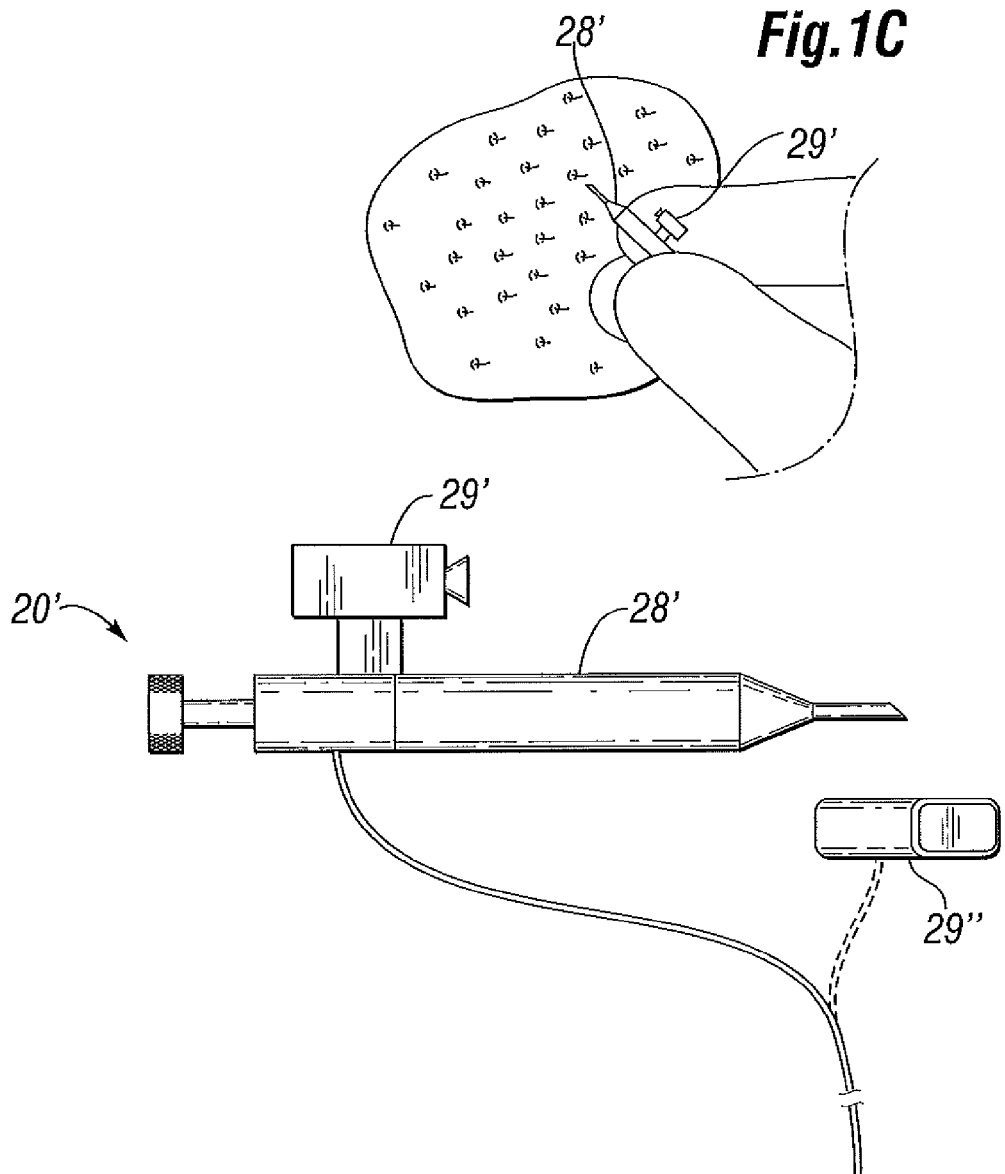
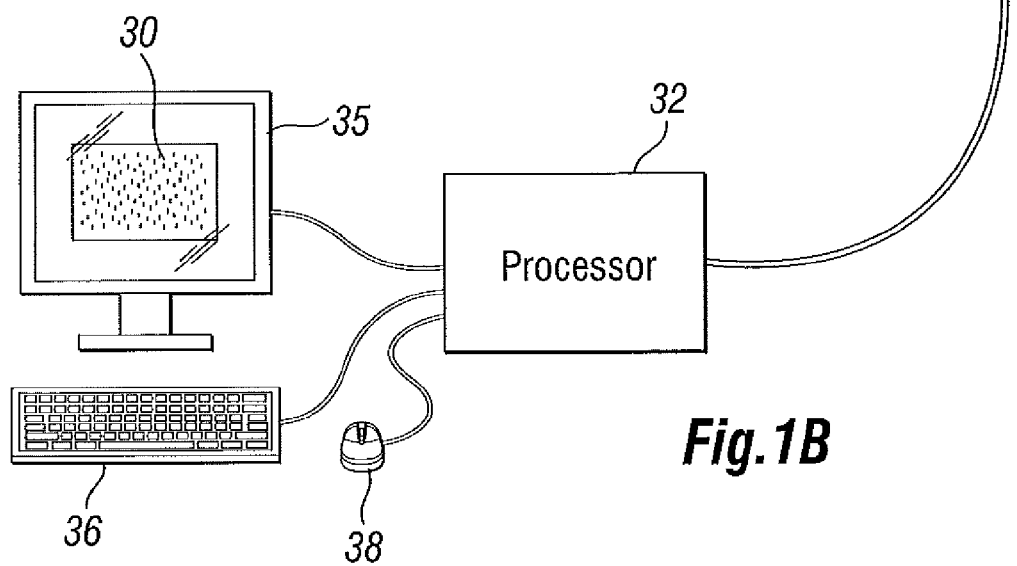
Fig.1C
Fig.1B

SYSTEMS AND METHODS FOR IMPROVING FOLLICULAR UNIT HARVESTING

CROSS REFERENCE TO RELATED APPLICATIONS

The present application claims priority to U.S. Provisional Patent Application Ser. No. 61/059,476, filed on Jun. 6, 2008, the disclosure of which is incorporated by reference herein in its entirety.

FIELD OF THE INVENTION

This invention relates generally to systems and methods for removing various biological tissue samples, including follicular units, from a body surface and, in particular, to methods and devices that utilize subsurface imaging to reduce potential damage to and maintain the integrity of the harvested hair follicles and/or tissue samples.

BACKGROUND OF THE INVENTION

There are various known tools and instruments for removing biological tissue samples from the body. For example, biopsy needles and punches are used when a small tissue specimen is required for examination, for example, to identify certain medical conditions. Another example of the biological tissue which is often desired to be removed or harvested is a hair follicle.

Hair transplantation procedures are well-known, and typically involve harvesting donor hair grafts from the "donor areas," for example, side and back fringe areas of the patient's scalp, or other body surfaces, and implanting them in a bald area ("recipient area"). Various techniques were developed over the years for harvesting donor hair grafts. Recently more physicians employ a technique called Follicular Unit Extraction ("FUE") that allows harvest of individual follicular units without a need to cut a strip of tissue from the patient's scalp.

An FUE method for harvesting follicular units utilizes a hollow needle punch having a cutting edge and an interior lumen with a diameter of for example, 1 mm. Generally, based on visualization of each follicular unit through magnifying optics, the needle punch advances along an axis of a follicular unit to be extracted. Thereafter, the follicular units are easily removed, e.g., using forceps, for subsequent implantation into a recipient site with a specially devised insertion needle. While it is a laborious procedure, it has distinct advantages over another known "strip harvesting" technique, like avoiding scarring associated with cutting a strip of scalp, reducing patient's discomfort, and reducing recovery time.

One of the limitations, however, of the FUE-based devices and methods is caused by the fact that the hair follicles do not maintain the same direction of growth under the skin as they do above the skin. Quite often a hair follicle significantly changes its direction or angle underneath the skin, and advancing the punch based on the visible portion of the hair follicle above the skin may result in follicle transection, damaging it or rendering it unusable for transplantation.

In general, attempts have been made to look at subsurface skin images up to about 1 mm when examining an epidermis layer of skin (e.g., for treating skin cancer). There are several publications that describe systems that have been used to allow for detection depth of up to 1.5 mm with some limited resolution to investigate at least approximate architecture of the skin lesions. Similarly, some work has been described for subsurface imaging at depths substantially greater than 5-6 mm, or to enhance the visibility of high-contrast blood vessels. U.S. Pat. No. 7,239,909 describes an imaging system to enhance visibility of subcutaneous blood vessels based on reflected infrared light. While certain developments were made to visualize high-contrast blood vessels which are usually located at least 5 mm or more below the skin level, there are no known systems or devices that provide clear images of low-contrast tissue/structures, for example, a hair shaft below the skin, and/or in some instances at least a portion of a bulb of a hair follicle below the skin.

Despite certain advances in improving the tools and systems for harvesting of biological tissue, such as hair follicles, there remains a need for a more efficient harvesting tool or system that increases the yield of usable harvested specimens by visualizing the subcutaneous structure and orientation of such specimens.

SUMMARY OF THE INVENTION

According to one aspect of the present invention, a method for determining subsurface information about a biological unit, such as a follicular unit, is provided. In one example, the method comprises imaging a follicular unit above a body surface using light of a first wavelength to form a first resultant image (or, in other words, imaging and processing the information to identify the follicular unit above the body surface), imaging the follicular unit above and below the body surface using either light of a second wavelength or having a different (for example, transverse) direction to form a second resultant image (or, in other words, imaging and processing the information to identify the follicular unit above and below the body surface). The first resultant image is subtracted from and/or combined with (which includes any method of subtracting and/or combining, such as by adding, deletion, subtraction, division or multiplication, as well by smoothing or sharpening any one or all of the relevant images) the second resultant image to obtain information about the follicular unit below the body surface. The information includes subsurface location and orientation of the follicular unit. In some embodiments of the invention, the method also provides for identifying a distance between relative portions of hair shafts of adjacent hair follicles below the surface from the images of the follicular units below the body surface, and based on that identified distance determining whether the adjacent hair follicles belong to the same follicular unit. Additional embodiments of the methods and systems of the present invention, as described below, may also provide for identifying a number of bulbs of a particular follicular unit based on the subsurface image information and classifying such follicular unit accordingly. In some embodiments, based on the obtained subsurface direction and/or curvature of the follicular unit, the method comprises dissecting and/or harvesting follicular unit from a body surface by aligning a certain way a removal and/or dissection tool with the follicular unit. The above-described methods for determining subsurface information may be performed in other embodiments, including those described herein, and in reference to the biological units other than follicular units, such, for example, biopsy samples or moles.

According to another aspect of the present invention, a method is provided for aligning (including orienting relative to) a harvesting tool with a subsurface orientation of a follicular unit on a body surface. In one embodiment, the method comprises obtaining an "above the surface" image of a follicular unit of interest, determining a location and/or orientation of the follicular unit above the body surface, aligning a harvesting tool and a portion of the follicular unit above the surface, identifying an offset of the position and/or orientation of the follicular unit below the surface with respect to the harvesting tool based on subsurface imaging, and repositioning the harvesting tool to align it with a portion of the follicular unit below the surface based on the offset. The method may further comprise dissection or harvesting the follicular unit. In some embodiments, identifying the offset may be accomplished, for example, utilizing optical coherent tomography, or ultrasound transducers, or infrared light, or other illumination sources. In some embodiments, the method for aligning, determining an offset, and repositioning of the tool may be based on stored data (including one or more stored images) and in some embodiments, repositioning may be based on the real-time data. Again, this and other methods and systems described below in reference to follicular units as an example, are also applicable to biological units other than follicular units.

Another method of the present invention for removing follicular units from a body surface, comprises first processing one or more images of a follicular unit both above and below the body surface. The images are stored, and a follicular unit removal tool is controlled based on the stored images. The follicular unit removal tool may be reoriented based on one or more of the images of the follicular unit below the body surface to remove the biological unit without damage or transection thereof. An image acquisition device such as one that senses light in the visible, infrared or near-infrared spectrum may be used. In some embodiments, the images include images below the body surface in the range of up to 5 mm, and preferably more than about 2 mm in depth.

A further aspect of the present invention is a method for dissecting hair follicles from a body surface that uses optical coherence tomography to obtain one or more images of a hair follicle. The one or more images may be enhanced to enable visualization of at least a portion of a curvature of a hair shaft beneath a body surface. The one or more images may be also enhanced to enable visualization of at least a portion of a bulb of the hair follicle beneath a body surface. Position and/or orientation of, for example, a hair follicle dissection tool may be controlled relative to the hair follicle below the body surface based on the one or more enhanced images to dissect the hair follicle from a surrounding tissue. In some embodiments, the depth of insertion of the hair follicle dissection tool may be controlled based on the one or more enhanced images. The orientation of the dissection tool may be changed as many times as necessary to follow the curvature of the hair follicle below the surface to dissect the hair follicle to keep it substantially intact. The hair follicle dissection tool can be operated to both dissect and remove the hair follicle for transplantation.

The one or more enhanced images may include an image below the body surface in the range of more than about 2 mm in depth. In a further aspect of the invention, the enhancement may be such that the one or more enhanced images have a signal to noise ratio of greater than 85 dB, and the hair follicle to a depth of greater than 2 mm below the body surface can be visualized to a resolution of smaller than 100 micrometers. Such enhancement may be achieved by decomposing the data from at least one of the one or more images into sub spatial frequency bands, processing each sub spatial frequency band to provide modified sub spatial frequency band data, and reassembling the modified sub spatial frequency band data to form an enhanced image with the desired signal to noise ratio. In yet another embodiment, it may be determined whether there is another (one or more) hair follicle having at least a portion of its hair shaft below the surface located within a predetermined distance from at least a portion of the below-the-surface hair shaft of the first hair follicle, and having those hair follicles with the hair shaft portions within the predetermined distance dissected as one follicular unit from a surrounding tissue. In another embodiment, it may be determined whether there is another hair follicle having at least a portion of its bulb within a predetermined distance from the at least a portion of the bulb of the hair follicle, and those hair follicles with the bulb portions within the predetermined distance are dissected as a single follicular unit from a surrounding tissue.

According to a still further aspect of the invention a system for dissecting hair follicles from a body is provided. The system comprises a processor which is configured to receive information from an image acquisition device. In one embodiment of the invention, the image acquisition device having utilized optical coherent tomography. The image acquisition device enables visualization of a hair shaft, including at least a portion of the curvature of the hair shaft below the surface. In some embodiments, at least a portion of a bulb of the hair follicle beneath the body surface may be visualized as well. The processor also comprises one or more modules for executing operations, the one or more modules comprising instructions for: determining the orientation of the hair follicle at least below the body surface based on the information received; and instructing movement of a hair follicle dissection tool relative to the hair follicle below the body surface based on the determined orientation to dissect the hair follicle from a surrounding tissue.

One or more of the modules may further comprise instructions to enhance the information received from the image acquisition device such that hair follicle at a distance of greater than 2 mm below the body surface can be visualized. One or more of the same or different modules may further comprise instructions to instruct changes in orientation of the dissection tool as many times as necessary to follow the curvature of the hair follicle below the body surface to dissect the hair follicle to keep it substantially intact.

The present invention also provides a system for removing biological units from a body surface. The system includes a biological unit removal tool, and one or more sensors, for visualizing at least below the body surface and obtaining images of biological units below the body surface. One or more of these sensors may also visualize above the body surface. In the case of multiple sensors, one of the sensors may be a digital camera, an infrared sensor, an ultrasonic sensor, or an optical coherence tomography (OCT) sensor, for example. In the case of a single sensor, different illumination methods may be utilized to achieve the desired images.

Another system of the present invention for visualizing a biological unit, such as a follicular unit on a body surface to assist in harvesting of the follicular unit, comprises an image acquisition device including a sensor for obtaining images of the follicular unit above the skin surface and a sensor for obtaining images of the follicular unit below the skin surface. A processor is configured to receive information from the image acquisition device, determine the location and orientation of the follicular unit above and below the body surface based on the images obtained by the image acquisition device, and instruct movement of a tool, for example a tool for harvesting follicular units, to align the tool with a portion of the follicular unit below the skin surface.

According to yet a further aspect of the present invention, a processor for visualizing a follicular unit on a body surface is provided. The processor may be configured to receive images of a follicular unit above a skin surface and below a skin surface, and includes routines to determine the location and orientation of the follicular unit above and below the body surface based on the images. In some embodiments, the processor is also configured to instruct movement of a tool for harvesting follicular units to align the tool with a portion of the follicular unit below the skin surface. In some further embodiments, the processor is also configured to identify from the received images a number of bulbs that the follicular unit has, and based on the number of bulbs determine a specific type of the follicular unit.

According to another aspect of the present invention, a method for dissecting hair follicles from a body is provided using ultrahigh frequency ultrasound to penetrate a body surface containing a hair follicle to a depth sufficient to obtain one or more images that allow to visualize at least a portion of a hair shaft, including a curvature of the portion of the hair shaft below the surface, and/or in some embodiments at least a portion of a bulb of the hair follicle below the body surface. A hair follicle dissection tool is controlled to be orientated relative to the hair follicle below the body surface based on the one or more images to dissect the hair follicle from a surrounding tissue.

Systems and methods of the present invention may be implemented for use with manual, partially automated and fully automated, including robotic, systems and procedures for removal of biological units, including hair harvesting and/or transplantation. Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIG. 1B is a schematic view of an example of a manual biological unit harvesting system of the present invention having subsurface imaging;

FIG. 1C is a detailed view of use of the manual harvesting system of FIG. 1B;

DETAILED DESCRIPTION OF THE PREFERRED EMBODIMENTS

Figure 1A:
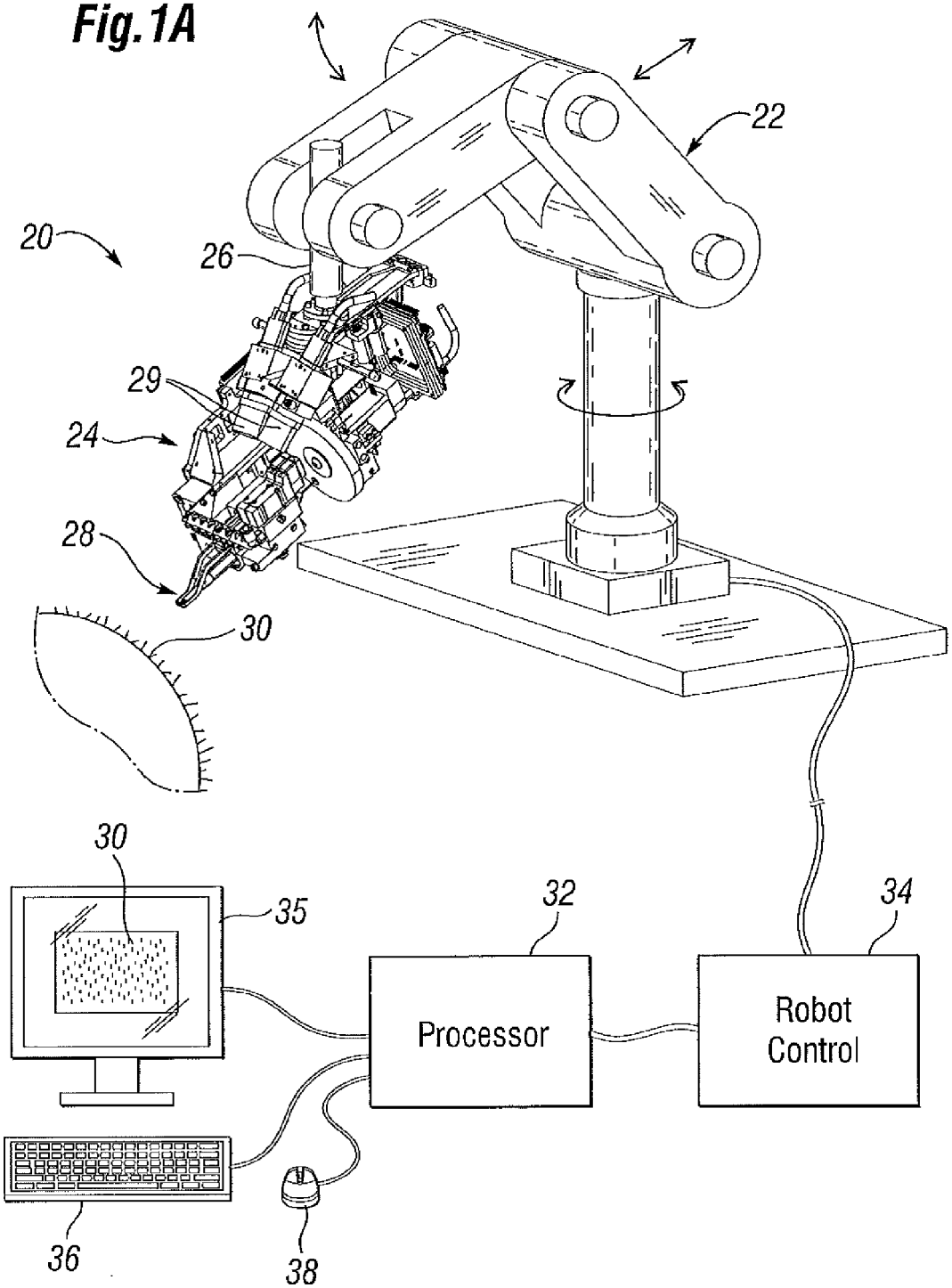
FIG. 1A is a schematic perspective view of an example of a robotic biological unit harvesting system of the present invention having subsurface imaging.

In the following Detailed Description, reference is made to the accompanying drawings that show by way of illustration some examples of the embodiments in which the invention may be practiced. In this regard, directional terminology, such as "top," "bottom," "front," "back," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system. The tools of the present invention could be used with the robotically-assisted systems and procedures. The adverb "automatically" when referring to use of a particular component of a system or a particular step in a process means that such step is accomplished autonomously, i.e., without real-time manual assistance.

The term "tool," or "biological unit removal tool," or "dissection tool" as used herein refers to any number of tools or end effectors that are capable of removing or harvesting various biological tissues, for example, follicular units ("FUs") from a body surface, and/or dissecting (or separating) them from a surrounding tissue. In general, however, the tools of the present invention may be useful for removing biological units other than FUs from a body surface. In this sense, a body surface (including any part of the body surface, such as a head, a trunk, limbs, etc.) can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), are typically sharpened, to cut and extract the tissue (e.g., hair follicle). Alternatively, the "tool" could be a laser, or ultrasonic energy device, or other energy device for removal of biological tissue, or ablation, or even complete destruction of such tissue. The terms "coupled," or "mounted" or "attached" as used herein, may mean directly or indirectly coupled, attached, or mounted through one or more intervening components.

"Biological units" as referenced in the present application include discrete units used in cosmetic, diagnostic, and dermatological procedures, for example, various tissues, including that extracted for biopsies or grafting, fat units, skin units, moles, etc. Examples of the biological units particularly useful with the present invention are hair grafts, or follicles, or "follicular unit(s)." Furthermore, "biological unit" may alternatively be referred to as "biopsy sample," "biopsy specimen," "biological tissue sample," or "biological tissue specimen." In a particular embodiment, the biological units are located at least partly within 1-5 mm below the skin.

As mentioned above, the term biological units encompasses a number of things, though the present invention is particularly useful in hair harvesting, to provide devices and methods for harvesting hair follicles, and/or follicular units (FUs). As such, the term follicular units (or FUs) will be used herein simply as an example for purposes of describing some embodiments of the present invention with the understanding that it represents more broadly biological units.

In particular, "follicular units" (also referred to as FU or FUs) are naturally occurring aggregates of 1-3 (and much less commonly, 4-5) closely spaced hair follicles that are distributed randomly over the body surface, such as a scalp. Each hair follicle has a bulb (a subsurface bottom-most portion that contains follicular stem cells and melanocytes). When harvesting a hair follicle, or a follicular unit for subsequent implantation in another area, it is important that the hair follicle be kept substantially intact. In some instance, substantially intact may comprise that the bulb of the hair follicle not be damaged. In other instances it may be sufficient to retain a predetermined quantity of the follicular stem cells and/or melanocytes, for example keeping intact in approximate terms the upper two thirds or the lower two thirds of the hair follicle. Scientists believe that the bulge of the hair follicle, which is situated in the vicinity of the sebaceous lobules, hosts stem cells as well. They also believe that stein cells reside in the outer root sheath and the bulb of the hair follicle. Keeping some or all of these stem cells with the hair follicle to be transplanted improves the probability of subsequent hair survival and growth. So keeping intact, for example, the upper two thirds of a hair follicle, which may include the bulge and a significant portion of the hair shaft, or the lower two thirds, which may include the bulb and up to and including the bulge, would increase the chances of a successful transplantation. It will be appreciated that in terms of a biological unit, the term intact will have various meanings dependent upon application, but will basically require that the biological unit retain its integrity for its application or purpose, and dictated by the same.

The follicular units may be classified, or "typed," based on the number of hair follicles in the unit and identified in shorthand as an "F1" for a single hair follicular unit, an "F2" for a two hair follicular unit and so on for follicular units with 3-5 hairs. It is desirable to identify follicular units based on the number of hairs in the follicular unit. For example, it is preferable to transplant certain classes of follicular units into specific regions of the scalp. For example, single hair follicular units (F1s) are commonly implanted along the hairline that frames the face. Follicular units with more than one hair (F2s, F3s, etc.) are commonly implanted in the mid-scalp and crown. While there are other ways to determine the type of follicular unit, determination of the type of the follicular units may be accomplished based on subsurface imaging. For example, in one instance, determination of the type of follicular unit may be accomplished based on a location of one or more hair follicle bulbs relative to each other. For example, by determining if at least a portion of the bulb of a first hair follicle is within a predetermined distance, typically less than about 1 mm, and in some instances even less than 0.8 mm, or less than 0.5 mm, from another portion of a bulb of a second hair follicle; one can decide if they belong to the same follicular unit (for example, F2), and also if the first and the second hair follicles should be dissected from the surrounding tissue as a single follicular unit, or as separate hair follicles. Alternatively, in some other instances the decision regarding dissecting and/or harvesting a plurality of follicles as one follicular unit may be based on subsurface imaging of at least portions of their relative hair shafts. For example, if at least a part of a hair shaft below the surface and up to a point where it exits the body surface of one hair follicle is in close proximity (for example, less than 1 mm, or less than 0.75 mm, or less than 0.5 mm) to a corresponding portion of a hair shaft below the surface and up to a point where it exits the body surface of another hair follicle, it may be determined that the first and second hair follicles should be dissected and/or harvested together as one follicular unit. In some cases, if the corresponding hair shafts run in close proximity along a portion within a depth up to about 4 mm below the body surface, it may be advantages to dissect and/or remove them as one unit.

The present invention encompasses utilizing various techniques for imaging low-contrast features and structures, in the region located up to 5-6 mm below the body surface, and especially including those located more than about 2 mm below the body surface (for example, between 2 and 3 mm), in order to determine the size, shape, position, and orientation of those low-contrast features and structures, such as subsurface follicular units, or more generally various biological units located at least partially within the same range below the body surface. The imaging requirement for hair follicles is, for example, that the hair shaft, including at least a portion of a curvature of the shaft beneath the body surface should be visible in the image; or, in another example, that the hair shaft and at least a portion of the bulb of the hair follicle beneath the body surface should be visible in the image. It should be appreciated that the depth at which the bulb of a hair follicle lies beneath the surface varies dependent upon what stage the hair follicle is in its life-cycle. This depth can vary from 1 mm to as much as 8 mm or more below the skin surface, typically being in the 1 to 5 mm range, and often in the 2 to 4 mm range. It is also known that the orientation or curvature of the hair shaft may change as it enters and traverses beneath the body surface. By visualizing of the hair shaft, including at least a portion of the hair shaft beneath the body surface, for example in the range of 1.5 to 2.5 mm, especially if there is a substantial curvature or change of its direction below the surface, a hair removal or harvesting tool can be guided at an optimal orientation to reduce the chances of transecting the hair shaft, thus enabling the harvested follicular unit to subsequently be transplanted to a desired location. Visualization of the hair shaft or its portion as described above, and in some instances also visualization of at least a portion of the bulb enables one to dissect or separate the hair follicle from the surrounding tissue and keep it substantially intact, without transection of the hair shaft and/or without transection of the bulb of the hair follicle, thus enabling the harvested follicular unit to subsequently be transplanted to a desired location. Without actual visualization beneath the body surface at the above-described depths, one has no option other than to guess the position, orientation and curvature of the hair shaft beneath the body surface, and to infer or guess the location and depth of the follicular bulb beneath the body surface. This ultimately leads to greater transection of hair shafts and/or bulbs.

By utilizing the methods and systems of the present invention, one is also able to select, based on the visualized hair shaft including at least a portion of a curvature of the hair shaft beneath the body surface, or based on the visualized hair shaft and at least a portion of bulb of the hair follicle, whether the hair follicle is desirable for dissection and removal for the purposes of transplantation or not. If disintegration of the hair follicle is observed, a choice may be made to select all alternative hair follicle for dissection and removal for the purpose of transplantation.

Various embodiments of the present invention employ subsurface imaging of the follicular units and other biological units/structures, including low-contrast and those located at Up to approximately 5-6 mm, including greater than 2 mm, below the body surface in harvesting systems, whether such systems are fully-automated (e.g., robotically controlled), semi-automated, or manually controlled. While the present invention is especially useful in robotically operated systems for dissecting and harvesting hair, it will also provide great benefit to a physician who removes follicular units using a manual FUE technique or with partially/fully automated hand-held tools, as it will guide the physician in adjusting an angle of insertion of the tool to avoid transecting or otherwise damaging the follicular unit or tissue to be harvested.

Various terms for imaging devices and systems are used herein. The terms image acquisition device and image sensor are synonymous, and the term camera is also considered to be an image sensor. Image sensors generate, receive and/or sense visible and non-visible images, such as within the visible spectrum, the infrared spectrum or ultrasonic waves. One example of the image acquisition device is one or more cameras, such as any commercially available cameras. Instead of a camera, it could be a video recording device (such as a camcorder) or any other image acquisition device. While stereo or multi-view imaging devices are very useful in the present invention, it is not necessary to employ such geometries or configurations. For example, the image acquisition device could be an analog TV camera that acquires an initial image which is then processed into a digital image (for example, via an analog-to-digital device like a commercial-off-the-shelf frame grabber) for further use in the present invention. The system of the present invention may include an illumination source, for example, an infra-red light emitting diode, a laser, or an ultrasound transducer. The system of the present invention typically incorporates an image processor. The image processor may comprise any device programmed and configured to perform the methods according to the present invention. One non-limiting example of a suitable image processor is any type of personal computer ("PC"). Alternatively, the image processor may comprise an Application Specific Integrated Circuit (ASIC) or Field Programmable Gate Array (FPGA). The image processor may be programmed with software configured to perform the methods of the present invention. The image processor may comprise one or more modules for executing operations and one or more modules may comprise instructions for performing various steps of the methods of the inventions described herein. For example, one module may contain instructions including determining location and/or orientation of the hair follicle below the body surface. The same or different module may contain instructions controlling movement of a tool (e.g. dissecting tool, or harvesting tool) relative to the location and/or orientation of the hair follicle below the body surface.

FIG. 1A is a schematic perspective view of an example of a robotic system 20 of the present invention for biological unit harvesting (and, optionally, implanting) with subsurface imaging. The system 20 includes a robotic arm 22 having a head assembly 24 mounted for rotation on a down tube 26 of the robotic arm. Various arrows are shown to illustrate the movement capabilities of the system 20. Furthermore, as will be seen below, motors and other such movement devices incorporated in the head assembly 24 enable fine movements of an operating tip of a tool 28 in multiple directions. The robotic system 20 further includes at least one imaging sensor 29 with subsurface imaging capabilities, as described below.

The operating tip of the tool 28 is shown positioned over a body surface 30, in this case a part of the patient scalp having hair follicles thereon. The tool 28 is any number of harvesting tools useful for removing follicular units from the body surface 30. A processor 32 acting, for example, through a robotic control 34 instructs the various movement devices of the robotic arm 22 and head assembly 24. The processor 32 may incorporate in some embodiments an image processor. As an example, the processor 32 may be any type of personal computer. Alternatively, the processor 32 may comprise ASIC or FPGA, or any other appropriate device. An operator monitors conditions and provides instructions through a monitor 35, keyboard 36, and mouse 38. A magnified image of the body surface 30 can be seen on the monitor 35.

FIGS. 1B and 1C show an alternative system 20' of the present invention for biological unit harvesting with subsurface imaging. Instead of a robotically- or automatically-controlled tool, the surgeon manipulates a handheld removal tool 28' to remove biological units. An imaging sensor 29', such as an infrared camera, may be mounted on the tool and provides real-time sub- and above-surface images to a processor 32 which generates images to a monitor 35. The surgeon can adjust the angle and position of the tool 28' based on the images sensed.

Alternatively, an optional ultrasound sensor 29" may be used, which is also shown attached to the system 20'. The ultrasound sensor 29" may be used prior to the biological unit removal step to map the subsurface configurations of select biological units, which information can then be referenced and shown on the monitor 35. In this arrangement, the imaging sensor 29' may be a standard visible light camera, or even stereo cameras.

The imaging sensor 29 (or 29') mounts on the system 20 (or 20') and is aimed toward the body surface 30. The imaging sensor 29 provides information about the hair follicles on the body surface 30, ultimately for controlling movement of the tool 28. For instance, as is known, the imaging sensor 29 can be stereo cameras that provide visible light images. An imaging subsystem in general associated with the system 20 may have one or more combined surface and subsurface imaging sensors, or it may include several independent imaging systems or sensors, including subsurface imaging that allows depiction of a part of the follicular unit underneath the skin or body surface. One example of the secondary sensor for subsurface imaging is an Optical Coherence Tomography (OCT) sensor, which may be incorporated into the system separate from the stereo cameras. Alternatively, infra-red sensors for providing subsurface images could be incorporated into the existing imaging camera or again could be added to the system as a separate device. In some applications, a separate imaging component for subsurface imaging is introduced, such as when using an ultrasound sensor. The ultrasound sensor generally has to touch the body surface for imaging, therefore, it could be incorporated into the system such that at least some part of it could extend and touch the relevant body surface. For example, an ultrasound sensor could be used in both automatically operated systems and in the manual procedures where physicians use hand-held devices. In the manual procedures, the ultrasound sensor may be incorporated into the hand-held device, or it could be a separate device that physician uses prior to harvesting to obtain subsurface images. In other embodiments an imaging sensor in the form of an ultrasound sensor may be attached to the robotic arm or the robotically-operated system of the present invention, for example, adjacent the harvesting tool 28. Measurements could be taken by the ultrasound device, for example, prior to harvesting off-line separately and then stored and used by the system.

Figure 2:
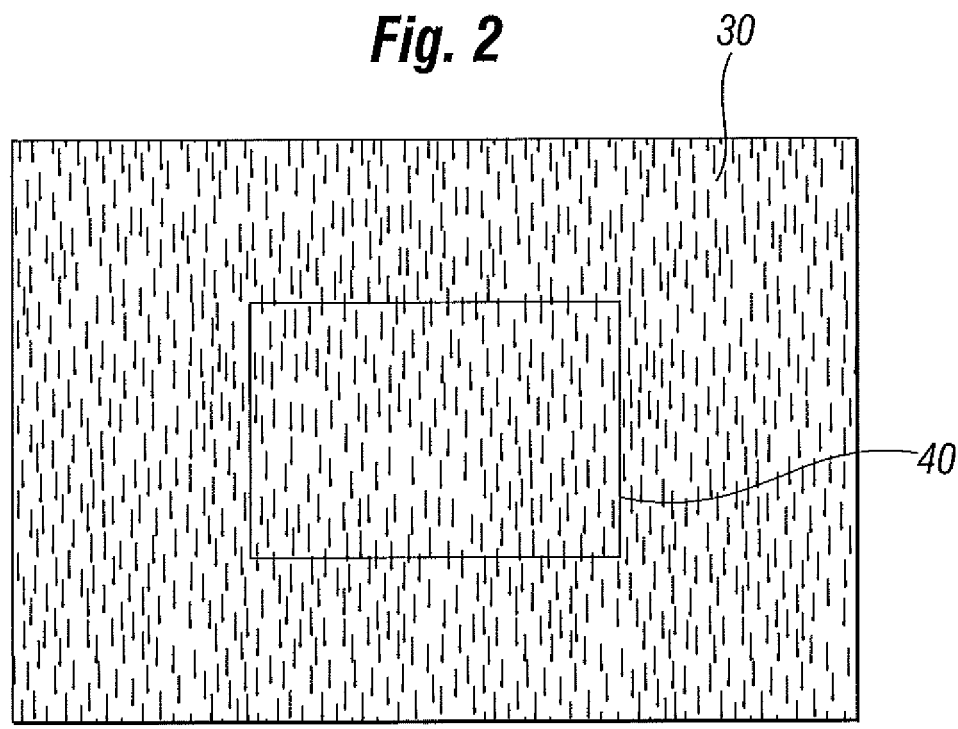
FIG. 2 depicts a camera image of hair follicular units in a region of interest on a body surface.

Usually, the robotics system 20 is initiated and calibrated so that the camera frame of the imaging sensor(s) 29 is aligned or oriented with respect to the tool frame of the harvesting or dissecting tool 28 of the present example. The image data is acquired by the imaging sensor 29 and processed by the processor to identify objects of interest in the camera frame. By way of example, FIG. 2 depicts a camera image of visible hair follicular units on the body surface 30 of FIG. 1A or 1B. From images of a region of interest 40 on the body surface 30, image segmentation and screening software residing, for example, in the computer identifies and selects one or more particular follicular units of interest for harvesting from the body surface.

Figure 3:
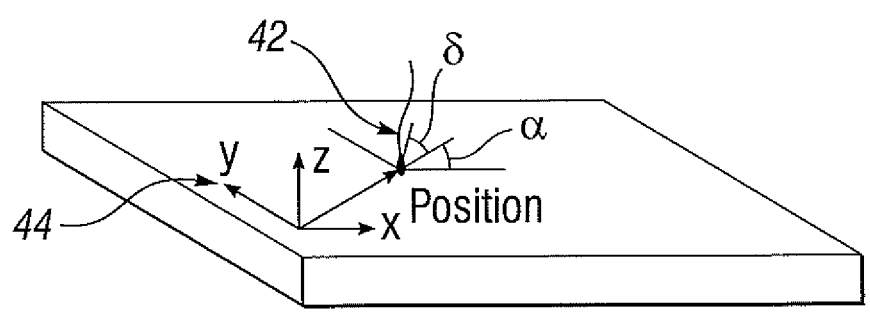
FIG. 3 illustrates position and orientation, i.e. defined by x,y offsets and in-plane and out-of-plane angles, of a hair follicular unit relative to the camera reference.

With reference to FIG. 3, the system 20 identifies a position of a selected hair follicular unit 42 in terms of its x,y offset coordinates 44 in the camera frame (the z axis being the camera optical axis which is in some embodiments aligned substantially orthogonal to the surface of the body surface 30 at the region 40). Generally, the system 20 may identify the location and orientation of follicular units relative to a donor area, for example, a scalp, including the angle from the scalp, so that the harvesting tool is adjusted accordingly to follow the orientation of the follicular unit above the skin until the tool touches the skin surface. The imaging system and the associated processing that enables subsurface imaging must determine similar information for below the skin. Complete information for above and below the skin may be determined up front and a sequence of tool movement above and below the skin could be pre-determined, or it could be determined on the go, or in real-time, as the tool moves. As mentioned above, for sensors that must contact the skin surface, like ultrasound, the information must be stored and referenced later.

With reference to image processing of the follicular units, unless the camera axis happens to be exactly aligned with the longitudinal axis of the follicular unit 42 (in which case the follicular unit will appear as a circular point representing an end view of the hair shaft), the image of follicular unit will be in the form of an elongate line having an "apparent" length that will depend on the angle of the camera frame relative to the follicular unit. Also, when the camera axis is not exactly aligned with the longitudinal axis of the follicular unit, a shadow of the follicular unit can typically be identified, which by definition is "attached" to the follicular unit at the body surface. Because of physical attributes of a hair follicular unit, its base (i.e., the end emerging from the dermis) can be readily distinguished from its tip as part of the image segmentation process. For example, the base portion has a different profile and is generally thicker than the distal tip portion.

Figure 4:
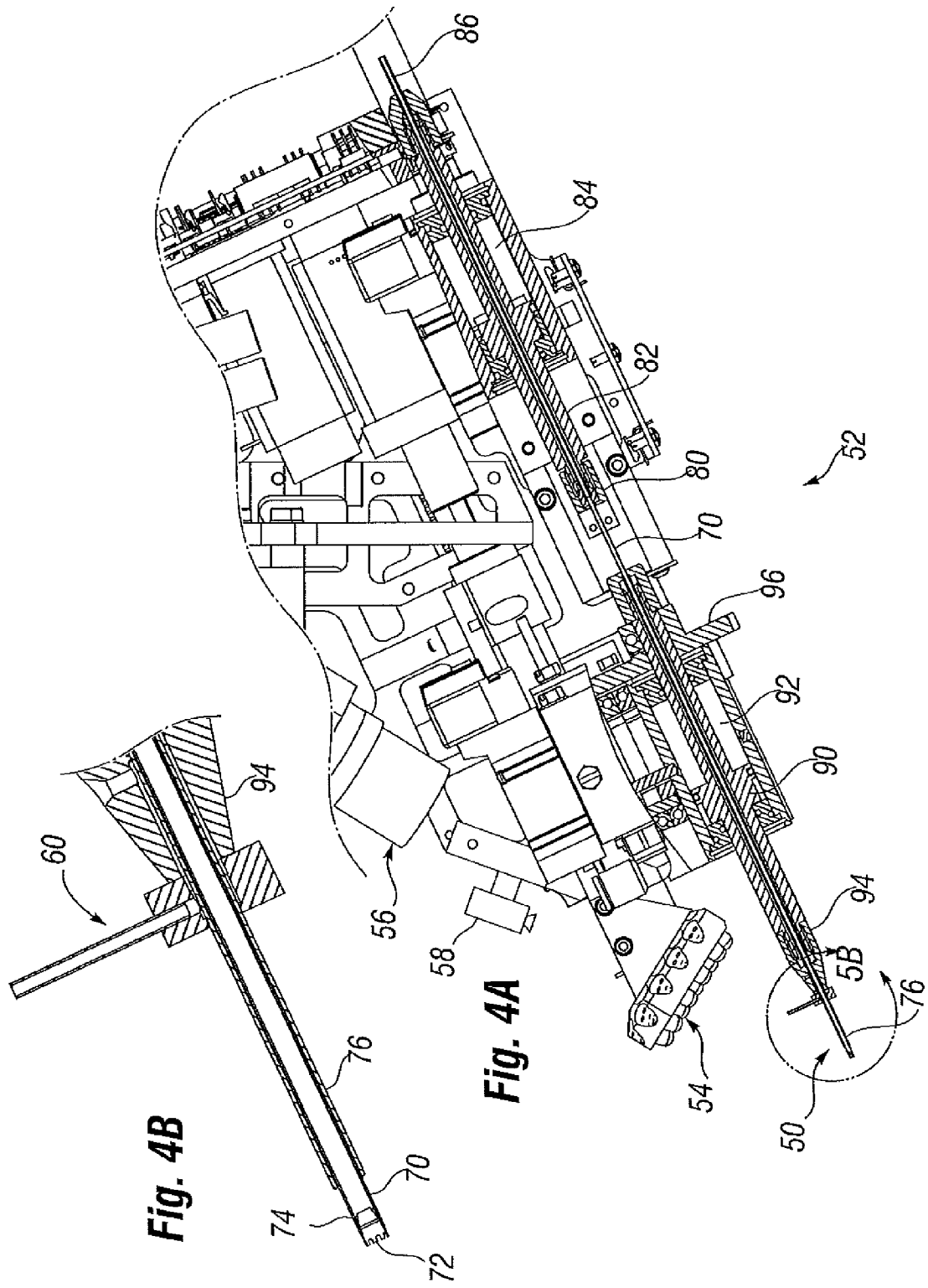
FIGS. 4A and 4B are perspective views of an example of an embodiment of a biological unit removal tool and imaging system incorporated in a robotically-operated system for hair removal.

A more detailed description of examples of follicular harvesting tools and assemblies is provided below in conjunction with FIGS. 4A and 4B, and in co-pending commonly assigned publication No. 2007/0106307, filed Apr. 28, 2006, and co-pending commonly assigned application Ser. No. 12/050,907, filed Mar. 18, 2008, both expressly incorporated by reference herein. FIGS. 4A and 4B are perspective views of an example of one embodiment of the biological unit removal tool 50 incorporated in a robotically-operated system 52 for hair removal and implantation. A bank of LEDs 54 illuminates a body surface in front of the system so that an imaging sensor 56 and a secondary sensor 58 aimed at the surface to obtain a clear picture for transmission back to a monitor (not shown). As mentioned above, the imaging sensors 56, 58 are one or more combined surface and subsurface imaging sensors, or it may include several independent imaging systems or sensors, including subsurface imaging that allows depiction of a part of the follicular unit underneath the skin. For instance, the sensor 56 can be stereo cameras that provide visible light images. Secondary sensors 58 for subsurface imaging may include OCT sensors or infra-red sensors. In the latter case, infra-red LEDs may be provided in the bank of LEDs 54. Various components are mounted for rotation or linear translation of the removal tool 50 at the distal end of the system. Stepper motors, air cylinders, and the like may be used, and will not be described in great detail herein.

The system may further incorporate a fluid (e.g., saline) delivery subsystem 60 as seen in FIG. 4B near the distal end of the removal tool. FIG. 4B also shows an inner tube 70 of the removal tool having a crown-shaped distal tip 72 and a retention device therein 74. Generally, the retention device 74 is used to assist in retaining a harvested follicular unit within the removal tool. An outer tube 76 of the removal tool surrounds the inner tube 70. Fluid may be delivered in a concentric space between the two tubes 70, 76 of the removal tool.

FIG. 4A also illustrates an example of a subsystem for moving the inner and outer tubes 70, 76 together and with respect to one another. In particular, the inner tube 70 extends along an axis of the subsystem in a distal direction and is held within a clamp 80 fixed with respect to a movable piston 82. The piston 82 reciprocates within a gas cylinder 84 depending on the pressure within the cylinder, which is controlled by a pneumatic subsystem that will be apparent to one of skill in the art. A distal end of an elongated flexible tube 86 abuts a proximal end of the inner tube 70 within a clamp 80, and defines a continuous extension of the lumen within the inner tube. Suction may be created within the inner tube 70, which continues through the flexible tube 86. The proximal end of the flexible tube 86 may engage a storage cartridge (not shown) for receiving and holding follicular units.

The outer tube 76 also reciprocates with a piston 90 within a gas cylinder 92. In particular, a leading end nut 94 holds the outer tube 76 fixed relative to the piston 90. In the illustrated embodiment, as seen in FIG. 4B, the fluid delivery subsystem 60 is located on a distal end of the nut 94. In addition, a gear 96 is keyed to and rotates the piston 90, and thus the outer tube 76. In this particular system, therefore, the inner and outer tubes 70, 76 translate coaxially with respect to one another (or in concert) and are displaced by independently controlled piston/cylinder mechanisms. Of course, the mechanisms for linearly displacing the two tubes 70, 76 may be linear motors or other alternatives. Furthermore, the outer tube 76 rotates with respect to the inner tube 70, and may be rotated in a constant or pulsed manner as it travels in a distal direction over the inner tube 70 and into the skin.

Figure 5:
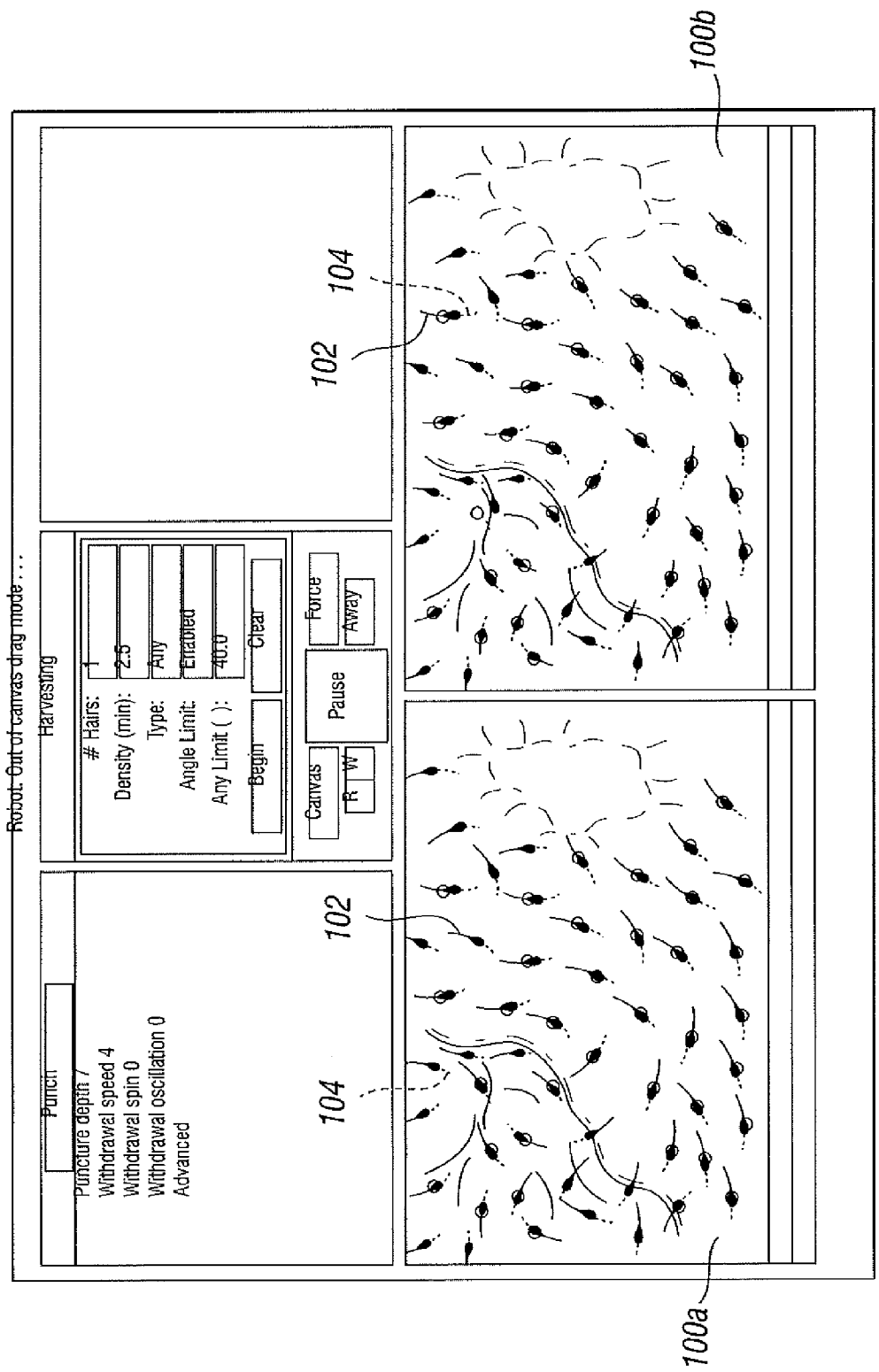
FIG. 5 is a snapshot of a monitor screen showing dual images from stereo camera pairs secured to the robotically-operated system of FIG. 4A, and information used to identify the position and orientation of multiple hair follicles for guiding a robotic arm and attached follicular unit removal tool.

Furthermore, the visible images from the stereo cameras may be combined with images from other sources. Such as infrared cameras. The monitor screen shot in FIG. 5 illustrates left and right images 100a, 100b from one or more such cameras. Each image shows the same area on the body surface, such as the region of interest 40 of FIG. 2. Because of the stereo images, processing software can determine depth information. For example, the system images multiple hair follicles 102 including subsurface portions 104. It should be understood that the image in FIG. 5 could also represent biological units 102 other than follicular units, including their subsurface portions 104.

In an embodiment of FIG. 4A, the bank of LEDs 54 produce light in the infrared spectrum, and the imaging devices 56 sense light in the infrared spectrum. The result is infrared lighting whose reflection is received in stereo. Although not shown, the bank of LEDs 54 may be mounted to the side so as to transversely illuminate the region of interest 40.

As will be appreciated by those skilled in the art, one can visualize below the skin surface by adjusting the lighting, filters on the cameras, and various image processing techniques. This is because the reflection and absorption of light by the skin surface will change based on the wavelength of light used. Further, the depth of penetration of the light itself into the skin also varies based on the wavelength. Understanding these basic properties of light, images of the subcutaneous portions of the follicular units (hair follicles) may be obtained using appropriate respective wavelengths of light, including both visible light spectrum and infrared, capturing the different wavelengths of light using different imaging filters, and subtracting and/or combining images during image processing. "Subtracting and/or combining" as used herein is by no means limited only to literal pixel subtraction and/or adding, but rather includes any method of combining data from, for example, image 1 and image 2 (by adding, deletion, subtraction, division or multiplication, including original pixel values or the logarithm of those pixel values, as well as by smoothing or sharpening any one or all of the relevant images) which makes details that are contained in either or both images more apparent. This approach enables one to visualize the hair shaft of the follicular unit, both outside the skin surface, as well as under the skin surface, including a curvature of the hair shaft beneath the skin, or all the way down to the bulb.

In general, different wavelengths of light penetrate to different depths and provide varying contrast in the skin. The present invention contemplates using different wavelengths of light to obtain different images of a biological unit embedded in skin, such as follicular units. By segmenting various images received at different depths, and combining and/or subtracting such images during image processing, the system is capable of isolating and visualizing the length, orientation and curvature of a follicular unit under the skin, including the information about location and a number of hair bulbs in a particular follicular unit.

The present invention contemplates imaging systems for determining information, such as shape, orientation, depth, direction of growth, etc., about a biological unit under the skin surface. Examples of the imaging contemplated with the present invention includes infrared or near infrared imaging, Optical Coherence Tomography (OCT), and High Frequency Ultrasound Imaging (HFUI). Particular examples of using these technologies are provided below.

Figure 6:
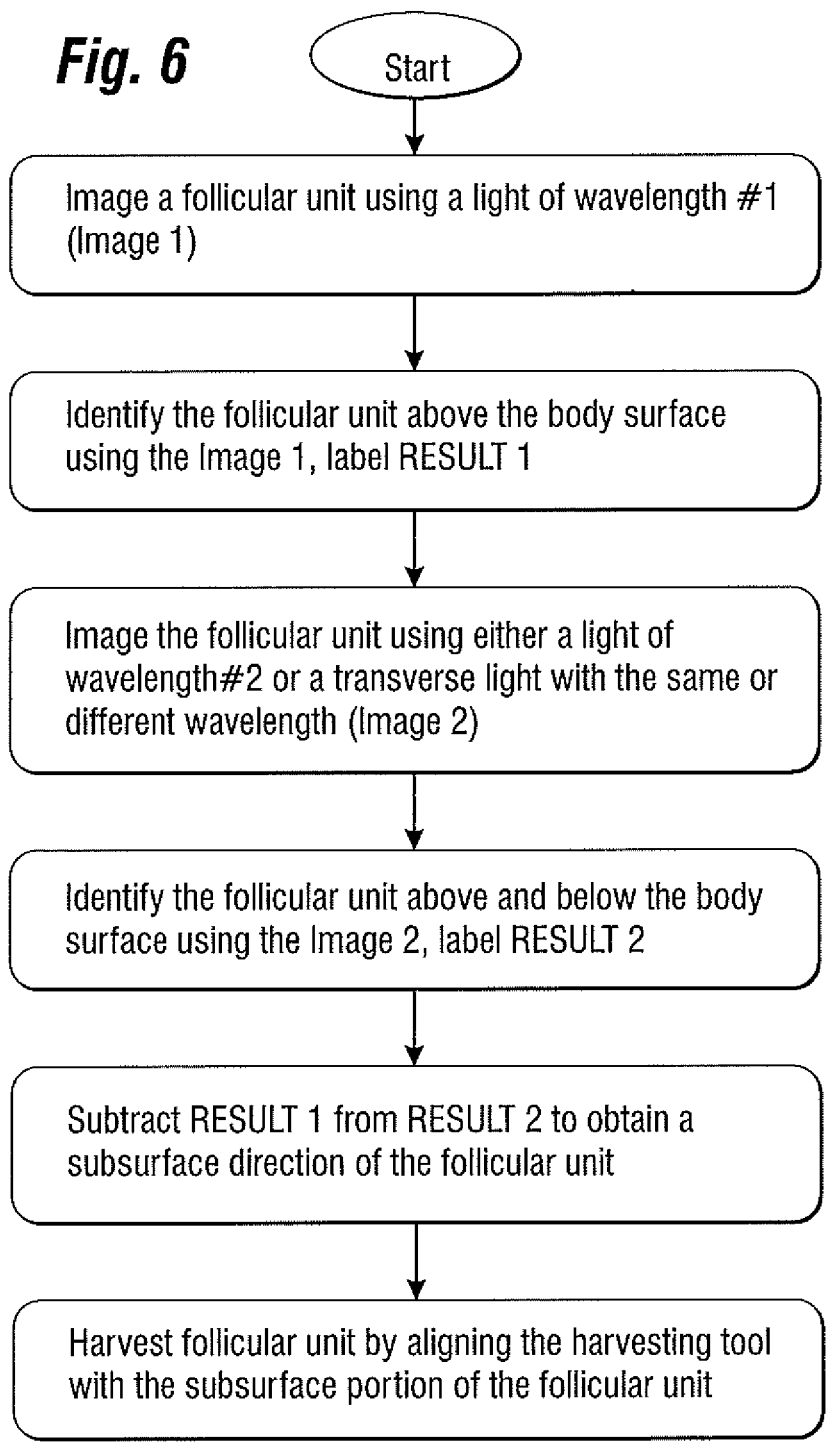
FIG. 6 is a flow chart describing an example of the image processing method according to one aspect of the present invention.

Subsurface imaging can be used with visible imaging for an enhanced understanding of the position and orientation of multiple hair follicles in a short amount of time. FIG. 6 is a flow chart describing one example of a method of the present invention using both above the surface and subsurface images. As the inventions described herein are also applicable to both substantially automated as well as manual procedures, it should be understood that procedure described in reference to FIG. 6 is equally applicable to either. For example, the hair follicle may be first imaged using a light of the first wavelength. Typically, it could be any wavelength in the visible spectrum and it is directed, for example, perpendicularly to the skin surface. For convenience, we can call this image Image 1. As was previously mentioned, any appropriate image acquisition device or image sensor may be used. The system, for example, through a processor as described in reference to FIGS. 1-5, processes the Image 1 to identify the size, shape, position, and orientation of the hair follicle outside (above) the skin surface, such as follicles 102 in FIG. 5. This can be called RESULT 1.

Then the follicular unit(s) of interest are imaged again, but this time using, for example, a light of a different wavelength, or it could be of the same wavelength but transverse (meaning that it is more or less parallel to the body surface that is imaged); alternatively, it could be both transverse and different wavelength, or it may differ in another property such as, for example, coherence. For convenience we will call this image as Image 2. Some examples of the Image 2 include using infrared or near infrared light. Again, these additional images are processed to determine and identify the characteristics of the follicular unit(s) above and below the skin surface, which can be termed RESULT 2. Subtracting and/or combining (as previously explained) RESULT 1 from RESULT 2 obtains, for example, the size, shape, position, direction and orientation of the subsurface portions 104 of the follicular unit (see FIG. 5), however other methods of subtracting and/or combining Image 1 and Image 2 may be used. Based on the results of the above-described process, the analyzed follicular unit may be dissected and/or harvested by positioning a harvesting tool, such as the tool 28 shown in FIG. 1, in alignment or in certain orientation with the direction of the follicular unit below the skin surface. Of course, the order of obtaining Image 1 and Image 2 may be reversed. In this case, if RESULT 1 identifies the follicular unit above and below the body surface and RESULT 2 identifies the follicular unit above the body surface, then RESULT 2 will be subtracted from RESULT 1.

More generally, with reference to the example of FIG. 6, a method for determining subsurface information about a biological unit, such as a follicular unit, is provided. The method of the example of FIG. 6 comprises imaging a follicular unit above a body surface using light of a first wavelength to form a first resultant image (or, in other words, imaging and processing the information to identify the follicular unit above the body surface), imaging the follicular unit above and below the body surface using either light of a second wavelength or having a different (for example, transverse) direction to form a second resultant image (or, in other words, imaging and processing the information to identify the follicular unit above and below the body surface). The first resultant image is subtracted and/or combined (as explained above) from the second resultant image to obtain information about the follicular unit below the body surface. The information includes subsurface location and orientation of the follicular unit. In some embodiments of the present invention, the method also provides for identifying a number of bulbs that belong to the same follicular unit from the image of the follicular unit below the body surface and based on the number of bulbs determining a specific type of the follicular unit, such as F1, or F2, etc.

In general, the subsurface image of each follicular unit or hair follicle can be used to pre-position the harvesting or dissecting tool, or to adjust the position during the operation of harvesting or dissection. For instance, the harvesting needle may be positioned and aimed prior to a single movement using the super- and subsurface information. Alternatively, the system may instruct the harvesting tool to align first with the "above the surface" portion of the hair follicle, and then change orientation if necessary based on the subsurface follicle angle. The subsurface data may further indicate a curvature in the subsurface follicle necessitating several orientation changes. These changes may be accomplished in real-time, as the tool moves, depending on the speed of the processor, and may be incorporated into automated or even manual systems. One example of a method for dissecting follicular units from a body comprises obtaining one or more images of a follicular unit comprising information on the location and/or orientation of the follicular unit both above and below the body surface. The location and/or orientation of the follicular unit above the body surface is then determined, and a follicular unit dissection tool controlled to be positioned and orientated relative to the position and/or orientation of the follicular unit above the body surface. An offset of a location and/or orientation of the follicular unit (e.g., a single hair follicle) below the body surface is identified with respect to the follicular unit dissection tool. The follicular unit dissection tool is then repositioned based on the identified offset to dissect the follicular unit from a surrounding tissue. In some embodiments at least one of the one or more images of the follicular unit are stored, and the offset is identified from the one or more stored images, and the follicular unit dissection tool is repositioned based on the offset identified from the one or more stored images.

In the alternative embodiment of the present invention, OCT-based imaging technology may be used in the system and method of the present invention. This technology can be used either in combination with the aforementioned subtracting and/or combining technique, or on its own. OCT works on the basis that when light falls on a tissue surface, some of the light penetrates the tissue and reflects off of various depths of the tissue. Even though a majority of the light is reflected off of the surface of the tissue, most of the reflected light is scattered. OCT captures only the light that is non-scattered, e.g. temporally-coherent light, and eliminates all the scattered light which is not temporally coherent. Separating temporally coherent light from non-temporally-coherent light is done by an instrument called optical interferometer, which is a part of the OCT instrument.

Research indicates that OCT can penetrate to various limited depths into skin depending on the wavelength of transmitted light. For example, Podoleanu (Podoleanu A G. Optical Coherence Tomography. Br J Radiol 2005; 78 (935): 976-988) indicates that OCT can penetrate to a depth of about 1.5 mm into skin with 800 µm light, and up to about 2 mm into skin with 1300 mm light. Any description in the literature, however, is limited to the region from 0 to about 1.5-2.0 mm, and more specifically under 0.9 mm below the body surface, and mostly directed to analyzing precancerous and cancerous skin structures.

The light penetration into highly scattering tissue, and therefore visibility, can be improved by the application of clearing agents, such as biocompatible and osmotically active agents, for example, glycerol, glucose, propylene glycol, polypropylene glycol (PPG), polyethylene glycol (PEG), and dimethyl sulphoxide (DMSO). Use of the above agents may induce an optical clearing effect, reduce optical scattering, and increase detection depth. A mixture containing any of the above-mentioned clearing agents may be topically applied to improve visibility.

Figure 9:
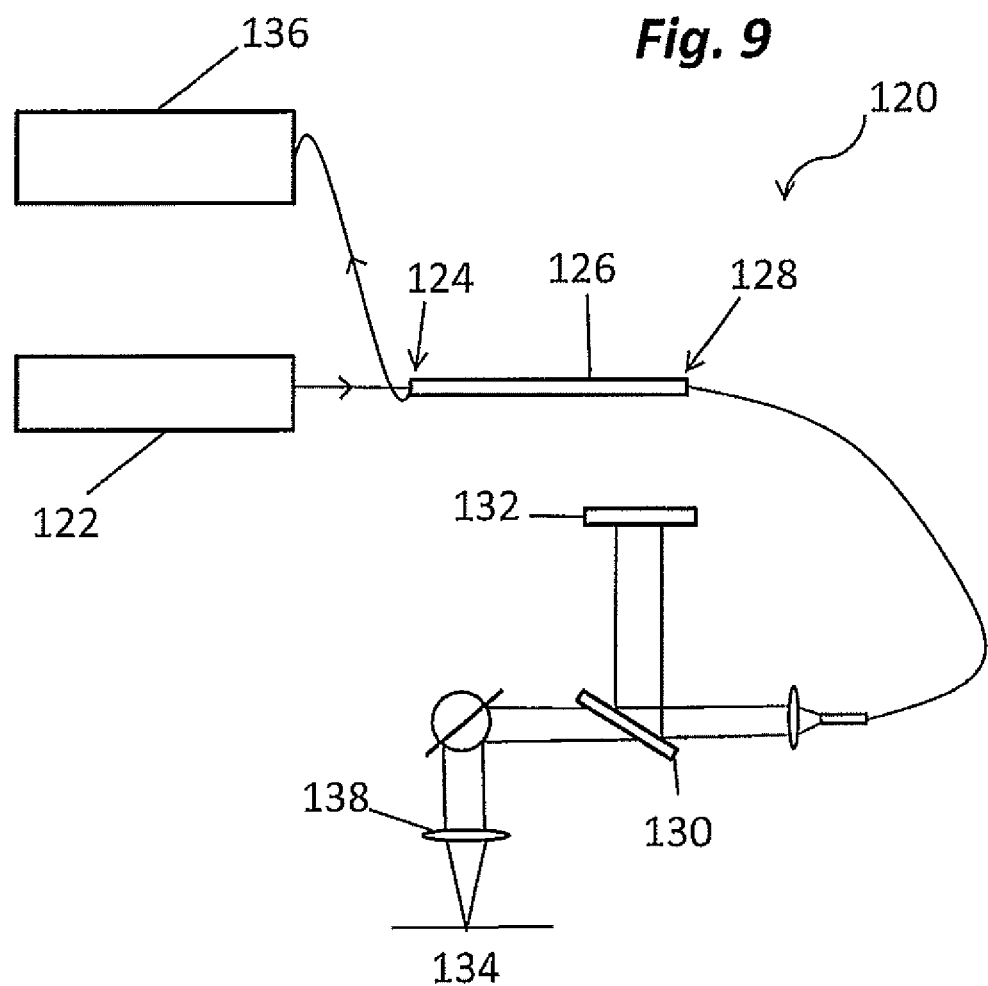
FIG. 9 is a schematic representation of an example of a spectral/Fourier-domain Optical Coherence Tomography system for hair follicle imaging according to the present invention.

An example of the OCT system 120 according to the present invention is illustrated schematically in FIG. 9. The OCT system 120 may be a spectrometer-based system composed of a light source, a super-luminescent light-emitting diode 122 that delivers broadband light into a circulator 126. Light entering port 124 of the circulator 126 is directed into port 128 and eventually split by a wedged window 130, with a split percentage in the range of 0.1-10 percent, preferably 1-6%, directed towards the reference arm 132, and the other remaining light continuing through towards the sample arm 134 (which in this example is the body surface). In order to maximize sensitivity, the percentage of light directed to the reference arm should be large enough that its associated noise is equal to or greater than the detector electronic noise. The use of a wedged window or beam splitter 130 (which comprises the center of the interferometer) enables detector saturation at the reference arm to be prevented and for a significant amount of source power to directly contribute to image information.

The OCT system 120 of the example of FIG. 9 utilizes a Spectral or Fourier-domain OCT technology, which offers an improved resolution and image-acquisition speed over the time-domain OCT technology. The system 120 may utilize a free-space interferometer to minimize dispersion concerns, however, it can be a fiber-based system. For the application to hair follicle dissection, a super-luminescent light-emitting diode 122 (SLD) which delivers broadband light is preferably employed. This light source 122 offers a high irradiance which supplies the need for a wide dynamic range and high detection sensitivity for imaging weakly reflecting structures (hair follicles) deep in tissue. To maximize tissue penetration depth, a super-luminescent diodes source 122 with a center wavelength in the range of 700-1700 nm is desirable. In one embodiment, a super-luminescent diode with a center wavelength in the range of 1250-1350 nm provides for a penetration depth of 2 mm or greater. Selection of a diode of 1250-1350 mm was found to minimize tissue scattering and absorption coefficients for this particular follicular unit application. The super-luminescent diode 122 also provides for a relatively wide bandwidth, in range of 20-10 nm.

In order to practice hair follicle dissection and/or removal methods using the OCT-based system of the invention, it is not only the tissue penetration depth that has to be considered, but also the maximum depth at which the system 120 itself can obtain images, and the resolution to which the images can be evaluated to enable hair follicle dissection to occur. The spectrometer resolution was selected such that the measurement range was greater than the expected tissue penetration depth. For example, for a maximum penetration depth in tissue on the order of about 2 mm, an imaging measurement depth greater than 2 mm, and preferably greater than 4 mm, is desired. For the example of the above-described Fourier-domain OCT system, the measurement depth is determined by the ability of the system 120 to resolve high frequency fringes, and on the optical properties of the tissue involved. Using the above system a measurement range of up to about 6 mm, for example, 5.7 mm can be achieved, however one should understand that the attainable measurement range depends on the refractive index of the tissue involved.

The axial resolution of the system 120 is determined by the coherence length of the source 122, which is in turn determined by the bandwidth. However, the bandwidth is limited by the spectrometer 136 of the OCT system 120, giving an axial resolution, for example, of about 30 micrometers at around 1300 nm. The lateral resolution of the OCT system 120 is completely decoupled from the axial resolution, and is determined by the lens 138 used to focus the beam on the tissue, or sample 134. Although a high numerical aperture lens typically gives the best lateral resolution, for this particular application of hair follicle dissection, in order to attain a reduction of multiple scatterings over the significant depth required, a smaller numerical aperture lens 138 may be used. This is particularly so since in-focus images deep into the tissue (for example, greater than 2 mm) are desired. Lenses 138 with a field of view of 1 mm or greater in any one direction, with greater than 3 mm offering better results, are utilized. These values provide a lateral resolution on the order of 30-35 micrometers.

In order to obtain good signal characteristics and to maximize in-focus imaging depth, the OCT system needs to be effectively aligned. Imaging depth is maximized by placing the focus inside the tissue to utilize the full depth of field. In one particular example, it was determined a depth of field of about 2.6 mm placed fully beneath the body surface would allow for visualizing and harvesting hair follicles (including the hair shaft and at least a portion of a curvature of the hair shaft, or in some embodiments the hair shaft and at least least a portion of the bulb) utilizing the system described herein.

In one embodiment, the selected detector may be an InGaAs array (136) which has readout line speeds of up to 47,000 lines per second. However, detectors with, for example, 10,000 lines per second and/or other different performance parameters may be employed as well The system sensitivity is defined as the ratio of the signal power generated by a perfectly reflecting mirror compared to the noise of the system. Typical signal to noise ratios in the range of greater than 85 dB and preferably greater than 100 dB are desired.

The OCT system as described herein provides one or more images of the hair follicle, including subsurface images. It enables improved visualization of a hair shaft or its portion, and/or at least a portion of the bulb of the hair follicle beneath the body surface, thus enabling the orientation of a hair follicle dissection tool or harvesting tool relative to the hair follicle below the body surface based on the one more enhanced images to dissect the hair follicle from a surrounding tissue, preferably substantially intact. In an embodiment of the invention, the orientation of the hair follicle dissection tool can be changed as many times as necessary to follow the curvature of the hair follicle below the body surface to dissect the hair follicle and to keep it substantially intact.

According to another aspect of the present invention, the images achieved by utilization of the above-described OCT-based system and methodology may be further enhanced by removing noise and improving contrast resolution. As a result, further improvement of visibility of low-contrast features at significant depths (for example, greater than 2 mm) beneath the body surface. In particular, speckle noise is bothersome to human observers. Prior to the enhancing process a two or three dimensional image of a hair follicle can be attained for example, by using a series of C-Scans or B-Scans. The enhanced processing comprises decomposing data from at least one of the one or more images into a number of sub spatial frequency bands, processing each sub spatial frequency band to provide modified sub spatial frequency band data, and reassembling the modified sub spatial frequency band data to form an enhanced image with the desired signal to noise ratio. By utilization of the enhanced processing, images below the body surface in the range of interest may be visualized, with the resolution at the higher depth values being less than at the resolution at lower depth values in some instances. For the purposes of hair follicle dissection or removal for transplantation, enhanced images below the body surface allow visualization of a substantial portion of the hair shaft, and/or in some embodiments at least a portion or the whole bulb of the hair follicle. For example, structures of interest located in some cases deeper than 2 mm can be visualized to a resolution of smaller than 100 micrometers, preferably smaller than 35 micrometers.

In some embodiments, pyramid decomposition imaging technique may be used to divide the different sub-bands to correspond to different spatial frequencies in the image. One form of pyramid decomposition uses "steerable filters" (Simoncelli 1995) which are known to preserve orientation information. In some embodiments, after Pyramid decomposition, the OCT images obtained utilizing the methods of the invention were found to contain horizontal noise texture due to speckle. Since the highest frequency sub-band may contain very little useful information, it may be completely suppressed in some embodiments, that is, the high frequency sub-band in the pyramid may be set to zero. The lowest frequency sub-band may contain much of the overall brightness variation (contrast) in the image. The original image contrast may be strong due to the large reflection from the skin. The lowest frequency sub-band may be reduced in amplitude to about 25% to 35% of its original value, around 30%, to minimize, but not eliminate the strong contrast. The remaining (mild-frequency) sub-bands are likely to contain both noise (including speckle) and useful image information. As mentioned earlier, in one example after Pyramid decomposition the OCT images were found to have noise due to speckle in one orientation, and the useful information was contained in another orientation. It was therefore desirable to suppress the noise in these bands while not eliminating signal information. This can be accomplished, for example, using a Gaussian coring technique, and making use of the results obtained by using a "steerable filters" (Simoncelli 1995) pyramid decomposition technique. In Gaussian coring, small amplitudes come through the function with less amplitude than in a linear coring function, in which small signals are suppressed while preserving larger signals. Large amplitudes come through the fiction with essentially the same amplitude of the linear coring function. For both orientations, low frequency signals at all amplitudes may be reduced. For the vertical orientation, very low amplitudes may be moderately suppressed. For horizontal orientations, small amplitudes may be suppressed completely, and moderate amplitudes may be suppressed moderately. In one embodiment, with sub-band data modified as described above, the final image was reassembled. Reassembling may be accomplished using any techniques known in the field.

In yet another embodiment of the present invention High Frequency Ultrasound, also known as HiFU or HFUS, is used. It works similar to standard ultrasound but using high frequency wavelengths, typically 20 MHz to 100 MHz. Ultrasound enables visualizing structures below the surface, as is frequently used in prenatal scanning. High frequency ultrasound resolves depths from a few millimeters to a centimeter. Again, the depth of interest with respect to hair follicles is approximately up to about 5-6 mm, in some cases from about 1 mm and up to 4-5 mm, and in some cases from more than 2 mm. Depending on the wavelength, the resolution and depth vary. As with any other ultrasound imaging, the sensor needs to be in contact with the surface of the skin. The ultrasound modality may be incorporated in either hand-held harvesting device or in robotic hair transplantation system as will be explained below.

First, follicles in a given area may be imaged with HiFU or HFUS using a series of B-scans, thus constructing a three-dimensional volume of a skin patch. The image processor processes the three-dimensional volumetric data to identify the direction of each follicle below the skin (i.e., portion 104 in FIG. 5). Each follicle's direction can be memorized in a table, or using a formula (by fitting the data), or by an average direction in a given area. This stored data can then be used as an offset at the time of harvesting the follicle. That is, the visible portion 102 of the hair follicle indicates a particular orientation, while the subsurface portion 104 may be slightly askew therefrom. Therefore, the instructions for the follicular unit removal tool may indicate to take into account both the above surface and subsurface follicle orientation.

As an example, a robotic hair transplantation system using the subsurface imaging system of the present invention may comprise any or all of the following subsystems:

A robot, including, for example, a robotic arm. The arm may have six degrees of freedom.

A mechanism to operate a harvesting tool, for example, a needle and/or punch for dissecting and/or removing hair/other biological units.

An imaging system, for example, stereo imaging, for follicle/tissue visualization outside (above) the skin surface.

A subsurface imaging system for follicle/tissue visualization below the skin surface. Subsurface imaging may be, for example, one of the three modalities described above, or a combination thereof, but is not limited to the examples of modalities mentioned. In some embodiments, the imaging systems for visualization of above and below the skin could be combined in one, or there may be only one imaging system for visualization of only the below the surface.

Processor, such as a computer to control various subsystems and provide the user interface. In some embodiments, the processor also incorporates the image processor.

The processor or the image processor of the system may process the two or three-dimensional volumetric data to identify the follicle position and orientation below the skill surface. That information is then used to direct and control a follicular unit dissection and/or removal tool, such as that seen in FIG. 1A, 1B, or 4A. When used for transplantation purposes, the information from the images is used to direct and control a follicular unit dissection and/or removal tool such that the follicular unit is dissected from the surrounding tissue and removed substantially intact, without transecting the hair shaft and/or without transecting the bulb of the hair follicle, thus enabling the dissected and/or harvested follicular unit to subsequently be transplanted to a desired location. Both orientation and depth of insertion of the dissection and/or removal tool can be controlled. In addition, the orientation of the tool can be changed as many times as necessary to follow the curvature of the hair follicle below the surface to dissect the hair follicle from the surrounding tissue and keep it substantially intact.

Figure 7:
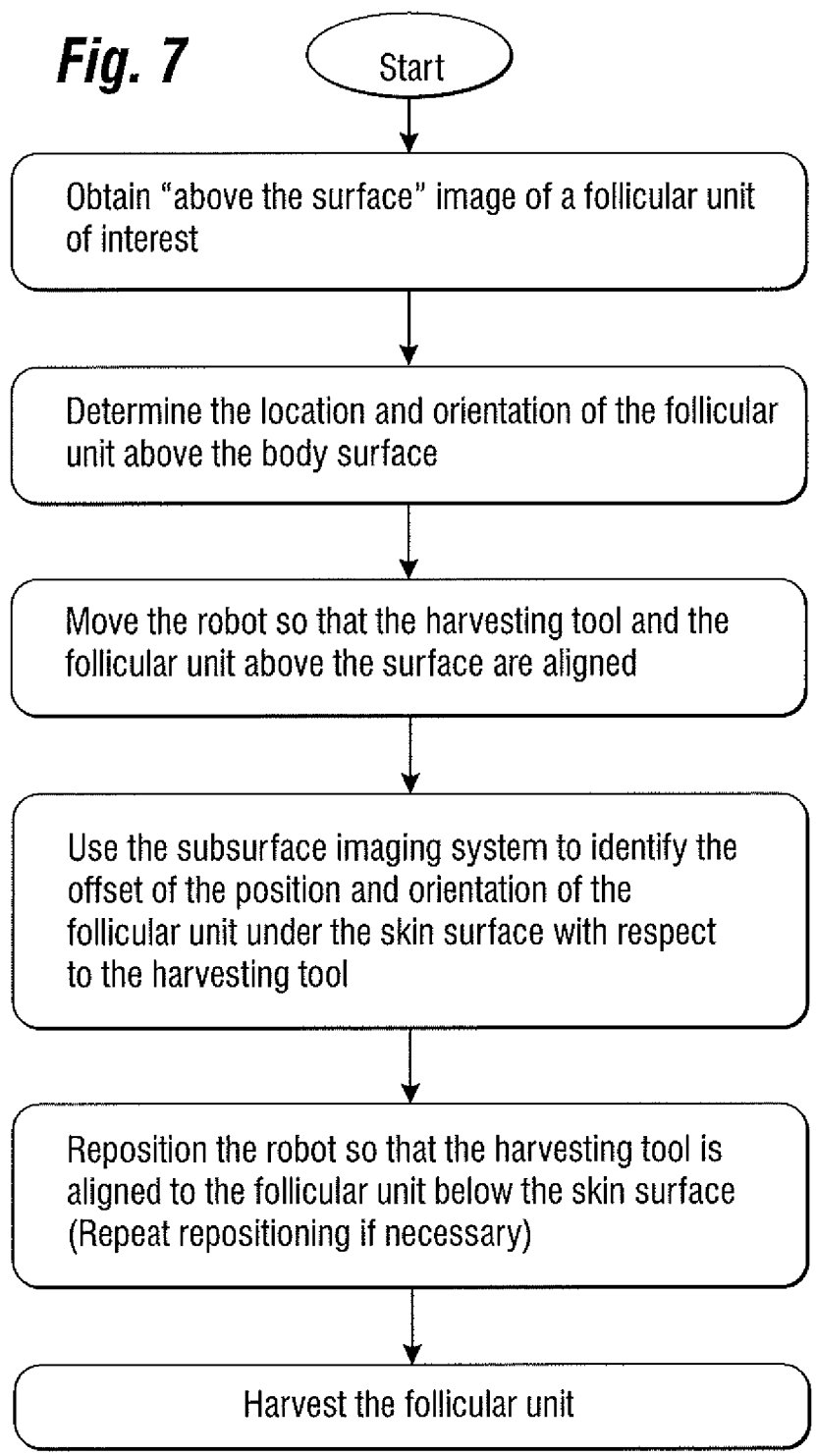
FIG. 7 is a flow chart describing the operation of a robotic hair harvesting system of the present invention that uses real-time subsurface imaging.

The flow chart of FIG. 7 describes one embodiment of the operation of robotic hair harvesting system that uses real-time subsurface imaging. As the present invention is also applicable to non-robotic procedures, it should be understood that the procedure described in reference to FIG. 7 would be adjusted accordingly for manual operation, such as eliminating all references to robotic arm/robot. First, in the above example, the image of the follicular unit (or units) of interest above the surface may be obtained. That may be accomplished by any technique known in the art. For example, in some embodiments a robotic arm (or a portable device in the physician's hand) with the attached image acquisition device may be positioned so that the harvesting region is in focus for the cameras. The image processor, such as any of those described in reference to FIGS. 1-5, processes the obtained image to identify the desired information about the follicular unit above the skin surface, such as the size, shape, position, and orientation of the hair follicle above the skin surface. Based on the determined location and orientation of the follicular unit of interest above the skin, the robotic arm with the attached harvesting tool (or a handheld tool in manual procedures) is moved so that the harvesting tool and the follicular unit above the surface are aligned.

As this embodiment is based on a real-time "on the go" imaging and alignment, additional images of the follicular unit(s) of interest using subsurface imaging, for example, OCT, may be obtained and processed to identify its characteristics under the skin surface. These images may be obtained before, after, or at the same time with aligning the harvesting or dissecting tool with the portion of the follicular unit above the surface. For example, in one implementation, an offset of the position and/or orientation of the follicular unit below the skin surface may be determined relative to the position of the harvesting or dissecting tool which was just aligned with the follicular unit above the surface. Based on the determined offset, the harvesting tool may be repositioned so that it is oriented relative to the follicular unit below the skin surface. The follicular unit now may be dissected and/or harvested based on the subsurface alignment so that the chance of damaging or transecting the follicular unit is substantially reduced. In some cases where the direction of the follicular unit below the surface changes several times, obtaining additional subsurface images of the follicular unit and repositioning of the harvesting tool may be repeated as necessary.

As mentioned above, the data on the subsurface characteristics of the follicles can be obtained immediately after the images are obtained, or first obtained and then stored. For instance, in the case of ultrasound (HFUS) and OCT as well, if it is more efficient, the images may be obtained and processed ahead of time and a series of offsets may be used. The offsets may be in the form of a lookup table, approximated by a formula, or an average in a given area of skin surface.

Figure 8:
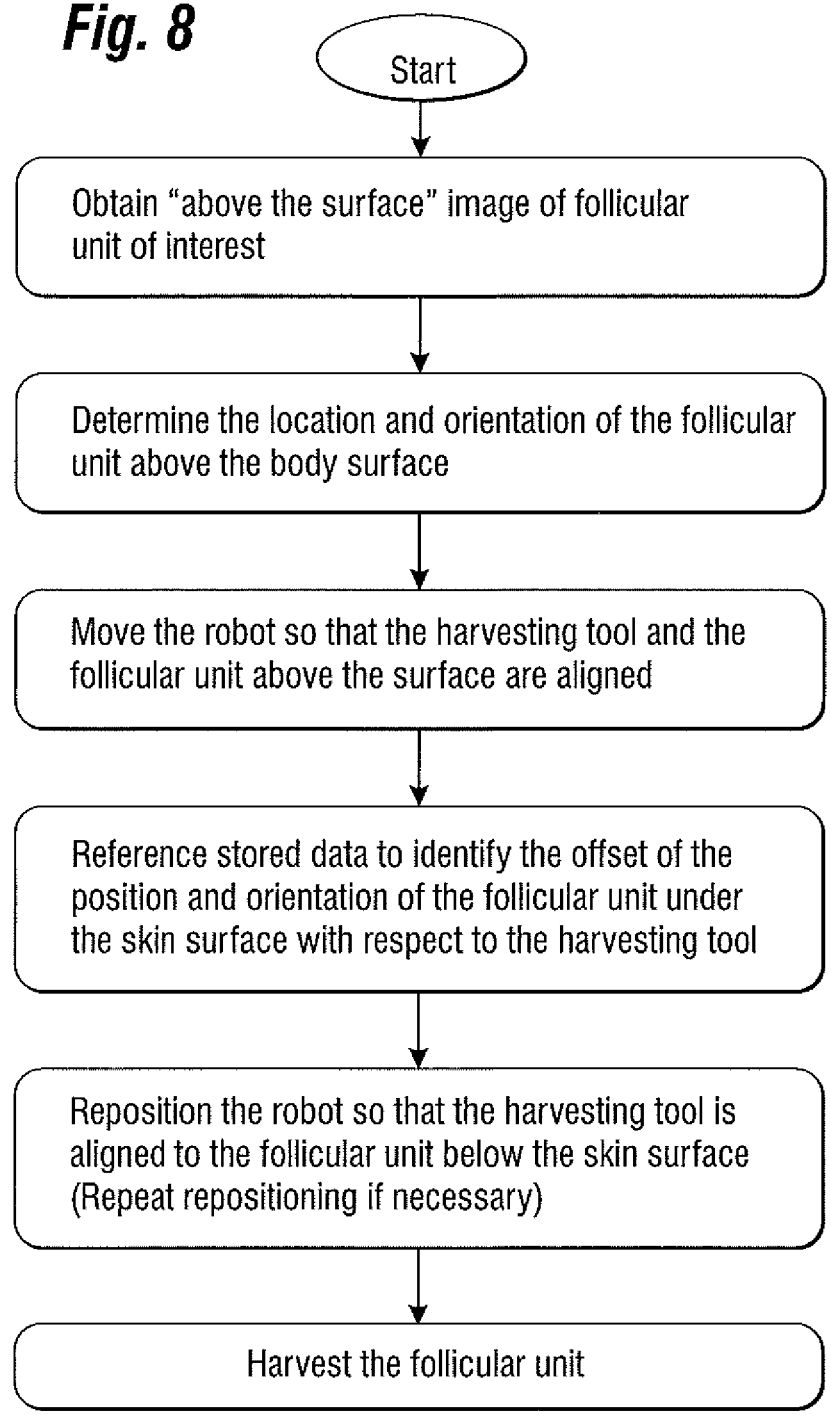
FIG. 8 is a flow chart describing the operation of a robotic hair harvesting system of the present invention that uses stored data on the subsurface character of follicular units.

FIG. 8 is a flow chart describing as an example the operation of a robotic hair harvesting system of the present invention that uses stored data on the subsurface character of follicular units. As in the previous example, since the present invention is also applicable to the non-robotic procedures, it should be understood that procedure described in reference to FIG. 8 shall be adjusted accordingly for the manual operation such as all references to robotic arm/robot shall be eliminated. As before, an image of the follicular unit(s) of interest above the body surface may be obtained. That may be accomplished by any technique known in the art. For example, in some embodiments a robotic arm (or a portable device in the physician's hand) with the attached image acquisition device may be positioned so that the harvesting region is in focus for the cameras. The image processor, such as any of those described in reference to FIGS. 1-5, processes the obtained image to identify the desired information about the follicular unit above the skin surface, such as the size, shape, position, and orientation of the hair follicle above the skin surface. Based on the determined location and orientation of the follicular unit of interest above the skin, the robotic arm with the attached harvesting tool (or a hand-held tool in manual procedures) is moved so that the harvesting tool and the follicular unit above the surface are aligned. The system then references subsurface imaging data, such as obtained previously with HFUS, and incorporates that data to reposition the robot so that the needle is aligned to the follicular unit below the skin surface. Based on the stored data about subsurface characteristics of the follicular unit, the tool may be repeatedly repositioned for alignment with various subsurface portions of the follicular unit, if necessary. The follicular unit is then may be dissected, and then harvested.

In general, one example of a system according to the inventions described herein comprises a processor which is configured to receive information from an image acquisition device, the image acquisition device enabling visualization of a hair shaft, including at least a portion of a curvature of the hair shaft beneath the body surface. The processor may also comprise one or more modules for executing operations comprising instructions for determining, for example, position or orientation of the hair follicle at least below the body surface based on the received information; and instructing movement of a hair follicle dissection tool relative to the hair follicle position or orientation below the body surface.

As will be appreciated by those skilled in the art, the methods of the present invention may be embodied, at least in part, in software and carried out in a computer system or other data processing system. Therefore, in some embodiments hardware may be used in combination with software instructions to implement the present invention.

The foregoing illustrated and described embodiments of the invention are susceptible to various modifications and alternative forms, and it should be understood that the invention generally, as well as the specific embodiments described herein, are not limited to the particular forms or embodiments disclosed, but on the contrary cover all modifications, equivalents and alternatives falling within the scope of the appended claims. For example, it will be appreciated by those skilled in the art that a particular feature or characteristic described in reference to one figure or embodiment may be combined as suitable with features or characteristics described in another figure or embodiment. Similarly, the invention is not limited to the use of a robotic system including a robotic arm, and that other automated and semi-automated systems may be utilized. Moreover, the system and method of the present invention can be a separate system used along with a separate automated transplantation system or even with a manual transplantation procedure.

While the invention has been described in its preferred embodiments, it is to be understood that the words which have been used are words of description and not of limitation. Therefore, changes may be made within the appended claims without departing from the true scope of the invention.

What is claimed is:

1. A method of dissecting hair grafts from a body comprising:
    using optical coherence tomography to obtain one or more images of a hair graft beneath a body surface;
    enhancing the one or more images to enable visualization of at least a portion of a curvature of a hair shaft of the hair graft beneath the body surface;
    positioning a hair follicle dissection tool relative to an above-the-surface portion of the hair graft;
    determining, using the one or more enhanced images, whether to change an orientation of the hair follicle dissection tool to account for the curvature of the hair shaft beneath the body surface; and
    if it is determined that a change in orientation is desirable, changing the orientation of the hair follicle dissection tool relative to the hair graft below the body surface to dissect the hair graft from a surrounding tissue.

2. The method of claim 1, further comprising controlling a depth of insertion of the hair follicle dissection tool based on the one or more enhanced images.

3. The method of claim 1, further comprising changing orientation of the dissection tool one or more times to follow the curvature of the hair shaft below the body surface to dissect the hair graft to keep it substantially intact.

4. The method of claim 1, wherein the one or more enhanced images include an image below the body surface in a range of more than 2 mm in depth.

5. The method of claim 1, wherein the enhancing comprises processing the one or more images to obtain a desired signal to noise ratio of greater than 85 dB, and improving contrast resolution so that the hair graft at a distance of greater than 2 mm below the body surface can be visualized.

6. The method of claim 5, wherein the hair graft at a distance of greater than 2 mm below the body surface can be visualized to a resolution of smaller than 100 micrometers.

7. The method of claim 6, wherein the hair graft can be visualized to a resolution of smaller than 35 micrometers.

8. The method of claim 1, wherein the enhancing comprises decomposing data from at least one of the one or more images into a number of sub spatial frequency bands, processing each sub spatial frequency band to provide modified sub spatial frequency band data, and reassembling the modified sub spatial frequency band data to form an enhanced image.

9. The method of claim 8, wherein the decomposing into a number of sub spatial frequency bands comprises decomposing the data by pyramid decomposition.

10. The method of claim 8, further comprising suppressing completely at least one sub spatial frequency band that contains substantially no useful image data.

11. The method of claim 8, further comprising reducing amplitudes within at least one sub spatial frequency band by more than twenty-five percent of their original values, thereby reducing noise whilst retaining some useful image data.

12. The method of claim 8, wherein at least one sub spatial frequency band is processed using a Gaussian coring function.

13. The method of claim 1, further comprising operating the hair follicle dissection tool to both dissect and remove the hair graft for transplantation.

14. The method of claim 1, further comprising:
    determining if there is at least a portion of a hair shaft of another hair follicle within a predetermined distance from the at least a portion of the hair shaft, and
    dissecting from the surrounding tissue the another hair follicle and the hair graft as one follicular unit if their respective portions of the hair shafts are within the predetermined distance.

15. The method of claim 1, wherein enhancing the one or more images further enables visualization of at least a portion of a bulb of the hair graft.

16. The method of claim 1, further comprising applying a clearing agent to the body surface to reduce optical scattering.

17. The method of claim 1, wherein the method is carried out by a robotic system, and the robotic system comprises a robotic arm.

18. The method of claim 17, wherein the robotic system comprises a light source in the range of 1250 to 1350 nm.

19. The method of claim 1, wherein a hair graft is a follicular unit, the method further comprising:
    determining from the one or more images a location and/or orientation of the follicular unit above the body surface;
    controlling position and orientation of the hair follicle dissection tool relative to the determined position and orientation of the follicular unit above the body surface; and
    identifying from the one or more images an offset of the location and/or orientation of the follicular unit below the body surface with respect to the hair follicle dissection tool.

20. The method of claim 19, wherein at least one of the one or more images of the follicular unit is stored, the offset is identified from the one or more stored images, and the hair follicle dissection tool is repositioned based on the offset identified from the one or more stored images.

21. The method of claim 1, further comprising selecting whether a hair graft is desirable for dissection based on the one or more images.

22. The method of claim 1, wherein using optical coherence tomography comprises using a spectrometer-based Fourier-domain device comprising a superluminescent diode and an InGaAs array detector.

23. The method of claim 1, wherein using optical coherence tomography comprises selecting an optical coherence tomography spectrometer whose resolution is such that its measurement range is greater than a predefined tissue penetration depth.

24. The method of claim 1 further comprising using one or more offsets in a form of a look up table to control the orientation of the hair follicle dissection tool.

25. A method for dissecting hair grafts from a body, the method comprising:
  using optical coherence tomography to obtain one or more images of a hair shaft of a hair graft, including at least a portion of a curvature of the hair shaft below the body surface;
  determining, based on the obtained one or more images, whether the hair graft is damaged and undesirable for dissection for purposes of transplantation; and
  if the hair graft is determined to be desirable, controlling orientation of a hair follicle dissection tool relative to the hair graft below the body surface based on the one or more obtained images to dissect the hair graft from a surrounding tissue.

26. The method of claim 25, wherein obtaining the one or more images comprises reducing noise and improving contrast resolution.

27. The method of claim 25, wherein controlling orientation of the hair follicle dissection tool comprises changing orientation of the dissection tool one or more times to follow the curvature of the hair shaft below the surface to dissect the hair graft to keep it substantially intact.

28. The method of claim 25, wherein the one or more images include an image below the surface in a range of more than 2 mm in depth.

29. The method of claim 25, further comprising applying a clearing agent to the body surface to reduce optical scattering.

30. A method for dissecting hair follicular units from a body, the method comprising:
  obtaining, using optical coherence tomography, one or more images of multiple hair follicles below a body surface;
  determining, using the obtained images, if at least a first portion of a first hair follicle below the body surface is located within a predetermined distance from at least a second portion of a second hair follicle below the body surface; and
  if the first portion is within the predetermined distance from the second portion, controlling orientation of a hair follicle dissection tool to dissect the first and second hair follicles from a surrounding tissue as one follicular unit.

31. The method of claim 30, wherein the predetermined distance is less than 1 millimeter.

32. The method of claim 30, further comprising:
  determining, using the obtained images, if at least a third portion of a third hair follicle is located within less than 0.8 millimeter of the first portion and the second portion; and
  if the third portion is within less than 1 millimeter of the first and second portions, controlling orientation of a hair follicle dissection tool to dissect the first, second and third hair follicles from the surrounding tissue as the one follicular unit.

33. The method of claim 30, wherein the first and second portions comprise at least part of bulbs of the first and second hair follicles.

* * * * *